US012589354B2

(12) United States Patent
Kanno et al.

(10) Patent No.: US 12,589,354 B2
(45) Date of Patent: Mar. 31, 2026

(54) ACIDIC GAS SEPARATION DEVICE, AIR PURIFIER, AIR CONDITIONER, AND ACIDIC GAS CONCENTRATION DEVICE

(71) Applicant: KURARAY CO., LTD., Kurashiki (JP)

(72) Inventors: Momotaro Kanno, Okayama (JP); Yoshihisa Inui, Okayama (JP); Hideharu Iwasaki, Osaka (JP)

(73) Assignee: KURARAY CO., LTD., Kurashiki (JP)

( * ) Notice: Subject to any disclaimer, the term of this patent is extended or adjusted under 35 U.S.C. 154(b) by 608 days.

(21) Appl. No.: 18/016,001

(22) PCT Filed: Jun. 30, 2021

(86) PCT No.: PCT/JP2021/024658

§ 371 (c)(1),
(2) Date: Jan. 13, 2023

(87) PCT Pub. No.: WO2022/019065

PCT Pub. Date: Jan. 27, 2022

(65) Prior Publication Data

US 2023/0271132 A1 Aug. 31, 2023

(30) Foreign Application Priority Data

Jul. 20, 2020 (JP) ................................ 2020-123383

(51) Int. Cl.
*B01D 53/02* (2006.01)
*A61L 9/04* (2006.01)
(Continued)

(52) U.S. Cl.
CPC .............. *B01D 53/32* (2013.01); *A61L 9/042* (2013.01); *A61L 9/16* (2013.01); *F24F 8/194* (2021.01);
(Continued)

(58) Field of Classification Search
CPC ............. A61L 2101/48; A61L 2209/14; A61L 2209/16; A61L 9/014; A61L 9/042;
(Continued)

(56) References Cited

U.S. PATENT DOCUMENTS

2006/0065522 A1 3/2006 Liu et al.
2013/0145935 A1 6/2013 Suzuka et al.
(Continued)

FOREIGN PATENT DOCUMENTS

EP 3673976 A1 7/2020
JP H07039752 A 2/1995
(Continued)

OTHER PUBLICATIONS

Extended European Search Report issued Nov. 28, 2023 in European Patent Application No. 21846501.1, 9 pages.
(Continued)

*Primary Examiner* — Christopher P Jones
(74) *Attorney, Agent, or Firm* — Element IP, PLC

(57) ABSTRACT

One aspect of the present invention is an acidic gas separation device including: an electrolyte layer; a pair of electrodes provided with the electrolyte layer interposed between the pair of electrodes; and a voltage application unit that applies a voltage between the pair of electrodes, wherein the pair of electrodes are gas permeable electrodes, and the electrolyte layer contains: at least one selected from the group consisting of high molecular weight redox compounds having a radicalization rate of 90% or more, high molecular weight redox compounds having a quinone group in a molecule, and high molecular weight redox compounds having an imino group in a molecule; and a nonvolatile electrolytic solution.

15 Claims, 3 Drawing Sheets

(51) Int. Cl.

| | |
|---|---|
| ***A61L 9/16*** | (2006.01) |
| ***B01D 53/32*** | (2006.01) |
| ***F24F 8/192*** | (2021.01) |
| *A61L 101/48* | (2006.01) |

(52) U.S. Cl.
CPC ....... *A61L 2101/48* (2020.08); *B01D 2252/30* (2013.01); *B01D 2257/302* (2013.01); *B01D 2257/304* (2013.01); *B01D 2257/404* (2013.01); *B01D 2257/504* (2013.01); *B01D 2259/818* (2013.01)

(58) Field of Classification Search
CPC . A61L 9/16; B01D 2252/30; B01D 2257/302; B01D 2257/304; B01D 2257/404; B01D 2257/504; B01D 2258/06; B01D 2259/818; B01D 2313/345; B01D 2325/04; B01D 2325/26; B01D 53/32; B01D 53/326; B01D 61/42; B01D 69/12; C01B 32/50; F24F 8/194; Y02C 20/40
See application file for complete search history.

(56) References Cited

U.S. PATENT DOCUMENTS

| | | | | |
|---|---|---|---|---|
| 2017/0113182 | A1 | 4/2017 | Voskian et al. | |
| 2018/0058729 | A1 | 3/2018 | Bahar | |
| 2018/0257027 | A1* | 9/2018 | Desai | C08J 5/2231 |
| 2019/0030485 | A1* | 1/2019 | Perry | B01D 53/326 |
| 2020/0023307 | A1 | 1/2020 | Voskian et al. | |
| 2020/0206682 | A1 | 7/2020 | Desai et al. | |
| 2021/0062351 | A1* | 3/2021 | Voskian | B01D 53/326 |
| 2022/0184552 | A1 | 6/2022 | Voskian et al. | |
| 2022/0307732 | A1 | 9/2022 | Bahar | |
| 2022/0339579 | A1* | 10/2022 | Voskian | B01D 53/326 |
| 2022/0362708 | A1 | 11/2022 | Voskian et al. | |

FOREIGN PATENT DOCUMENTS

| | | | |
|---|---|---|---|
| JP | 2007045856 | A | 2/2007 |
| JP | 2015036128 | A | 2/2015 |
| JP | 2018001131 | A | 1/2018 |
| JP | 2021102198 | A | 7/2021 |
| WO | WO-2015125694 | A1 | 8/2015 |
| WO | WO-2020017631 | | 1/2020 |

OTHER PUBLICATIONS

International Search Report issued Sep. 7, 2021 in PCT/JP2021/024658 (with English translation), 4 pages.

International Preliminary Report on Patentability and Written Opinion issued Feb. 2, 2023 in PCT/JP2021/024658 (with English translation), 12 pages.

* cited by examiner

ACIDIC GAS SEPARATION DEVICE, AIR PURIFIER, AIR CONDITIONER, AND ACIDIC GAS CONCENTRATION DEVICE

TECHNICAL FIELD

The present invention relates to an acidic gas separation device, an air purifier, an air conditioner, and an acidic gas concentration apparatus.

BACKGROUND ART

Carbon dioxide, known as an acidic gas, is not only a substance that is widely present on the earth and accounts for about 0.04% in the atmosphere, but is also widely used in industry. Examples of the method for utilizing carbon dioxide include foaming gases such as carbonated beverages, bath agents, and fire extinguishing agents, dry ice used for cooling or the like, and air for emergency replenishment to bicycle tires. In addition, carbon dioxide can also be used as an extraction solvent for extracting caffeine and the like by being brought into a supercritical state. Carbon dioxide is also used for a laser used for processing in the industrial field, a carbon dioxide laser used for a medical laser scalpel, and the like. Furthermore, carbon dioxide may be used as the refrigerant of the compressor in place of fluorocarbon refrigerants. Also in the agricultural field, carbon dioxide is used, for example, in forcing cultivation of strawberries and carbon dioxide fertilization for accelerating the growth of plants such as waterweeds in an ornamental water tank. Carbon dioxide is also used for controlled atmosphere (CA) storage of fresh agricultural products.

Since carbon dioxide is used in various fields as described above, a method for obtaining carbon dioxide by, for example, separating carbon dioxide from a gas containing carbon dioxide, such as air has been required. Carbon dioxide is also said to be a causative substance of global warming. For this reason as well, it is required to separate carbon dioxide from a gas containing carbon dioxide and use carbon dioxide.

Furthermore, human activity varies greatly depending on the concentration of carbon dioxide in the room, and it is generally said that attention is reduced when the concentration of carbon dioxide exceeds 1,000 ppm. For this reason, it is required to reduce the concentration of carbon dioxide also in a closed space such as a space in an automobile, a living room, and the like. However, it is often difficult in real life to reduce the concentration of carbon dioxide by periodically performing ventilation for reasons such as avoiding a change in indoor temperature and odor. Also from such a viewpoint, there is a demand for a technique for reducing the concentration of carbon dioxide in a room by separating carbon dioxide from a gas containing carbon dioxide and preferentially exhausting the separated carbon dioxide.

As a method for separating carbon dioxide from a mixed gas containing oxygen and carbon dioxide, such as air, various methods have been proposed. Examples of the separation method include a method in which carbon dioxide in the air is adsorbed using a carbon dioxide adsorbent, and then the carbon dioxide which has been adsorbed to the absorbent is desorbed from the absorbent to separate the carbon dioxide from the air. Examples of the adsorbent that adsorbs carbon dioxide include activated carbon, an amine-based solvent, and an aqueous potassium carbonate solution. As the method for separating carbon dioxide using an adsorbent, more specifically, a pressure swing adsorption (PSA) method is exemplified in which carbon dioxide is adsorbed to an adsorbent under high pressure, and then the pressure is reduced to cause carbon dioxide to be desorbed from the adsorbent. Examples of the adsorbent used for separating carbon dioxide by the PSA method include the adsorbent described in Patent Literature 1, and the like.

Patent Literature 1 describes a carbon dioxide adsorbent including a composition in which 2 to 80 equivalent % of sodium ions of a sodium-containing aluminosilicate have been ion-exchanged with barium ions.

In addition, it is also required to separate not only carbon dioxide but also other acidic gases such as NOx, SOx, and hydrogen sulfide from a gas containing an acidic gas. Examples of the apparatus that adsorbs and separates an acidic gas such as carbon dioxide include the apparatuses described in Patent Literatures 2 and 3.

Patent Literature 2 describes an acidic gas adsorption/desorption device including: an acidic gas adsorption/desorption layer containing a compound that enables adsorption and desorption of an acidic gas through its oxidation and reduction and a substrate; and a pair of electrodes sandwiching the acidic gas adsorption/desorption layer therebetween.

Patent Literature 3 describes a carbon dioxide separation apparatus including: an electrolyte layer; a pair of electrodes provided on the electrolyte layer with the electrolyte layer interposed therebetween; and a voltage application unit that applies a voltage between the pair of electrodes, in which the pair of electrodes are gas permeable electrodes, and the electrolyte layer contains: an electrolytic solution capable of dissolving carbon dioxide; and a redox compound having an N-oxy radical group in the molecule.

Patent Literature 1 discloses that an adsorbent having a high selection ratio of carbon dioxide and a large absorption capacity even under a condition of a large amount of moisture can be provided. Patent Literature 1 also discloses that this adsorbent can be suitably used for separating and concentrating carbon dioxide by the PSA method.

In such a method for separating carbon dioxide by the PSA method, for example, the method using an adsorbent or the like described in Patent Literature 1, pressurization and depressurization are required as described above. In addition, in the case of a method for separating carbon dioxide using an adsorbent, not only an operation of adsorbing carbon dioxide to the adsorbent but also an operation of desorbing carbon dioxide adsorbed to the adsorbent, for example, a heat treatment or the like is required even in a method other than the PSA method. For this reason, the method for separating carbon dioxide using an adsorbent sometimes requires a relatively large amount of energy or a relatively large apparatus.

Patent Literature 2 discloses that separation and desorption of an acidic gas can be performed in a solid state. Specifically, in the apparatus described in Patent Literature 2, first, a voltage is applied between electrodes to cause the acidic gas adsorption/desorption layer to adsorb the acidic gas. Thereafter, the voltage applied between the electrodes is inverted such that the current flowing through the acidic gas adsorption/desorption layer disposed between the electrodes is in the reverse direction to that at the time of adsorption, to thereby cause the acidic gas to be desorbed from the acidic gas adsorption/desorption layer. As described above, in the apparatus described in Patent Literature 2, it is necessary to invert the voltage applied between the electrodes when the acidic gas is adsorbed to the acidic gas adsorption/desorption layer and when the adsorbed acidic gas is desorbed from the acidic gas adsorption/desorption layer. In the apparatus described in Patent Literature 2, even if it is attempted to separate the acidic gas, it is necessary to invert the voltage applied between the electrodes as described above. For this reason, the apparatus described in Patent Literature 2 cannot continuously separate the acidic gas from the gas containing the acidic gas. Therefore, in the apparatus described in Patent Literature 2, as in the case of using the adsorbent described in Patent Literature 1, a relatively large amount of energy is required or a relatively large apparatus is required in some cases.

On the other hand, Patent Literature 3 discloses that carbon dioxide can be separated only by applying a voltage between a pair of electrodes without inverting the voltage applied between the electrodes, and thus carbon dioxide can be easily separated from a gas containing carbon dioxide. Therefore, when the apparatus described in Patent Literature 3 is used, it is not necessary to invert the voltage applied between the electrodes, and thus carbon dioxide can be continuously separated from a gas containing carbon dioxide. Furthermore, carbon dioxide can be easily separated from a gas containing carbon dioxide by a small apparatus.

Such an apparatus capable of separating an acidic gas such as carbon dioxide is required to more efficiently separate an acidic gas from a gas containing an acidic gas, and at the same time, to be able to repeatedly separate an acidic gas from a gas containing an acidic gas such as carbon dioxide over a long period of time.

CITATION LIST

Patent Literatures

Patent Literature 1: JP H7-39752 A
Patent Literature 2: JP 2015-36128 A
Patent Literature 3: JP 2018-1131 A

SUMMARY OF INVENTION

The present invention has been made in view of such circumstances, and an object of the present invention is to provide an acidic gas separation device capable of easily separating an acidic gas from a gas containing an acidic gas and repeating the separation over a long period of time. Another object of the present invention is to provide an air purifier, an air conditioner, and an acidic gas concentration apparatus including the acidic gas separation device.

One aspect of the present invention is an acidic gas separation device including: an electrolyte layer; a pair of electrodes provided with the electrolyte layer interposed between the pair of electrodes; and a voltage application unit that applies a voltage between the pair of electrodes, wherein the pair of electrodes are gas permeable electrodes, and the electrolyte layer contains: at least one selected from the group consisting of high molecular weight redox compounds having a radicalization rate of 90% or more, high molecular weight redox compounds having a quinone group in a molecule, and high molecular weight redox compounds having an imino group in a molecule; and a nonvolatile electrolytic solution.

The above and other objects, features, and advantages of the present invention will become apparent from the following detailed description and the accompanying drawings.

DESCRIPTION OF EMBODIMENTS

Hereinafter, embodiments according to the present invention will be described, but the present invention is not limited thereto.

Figure 1:
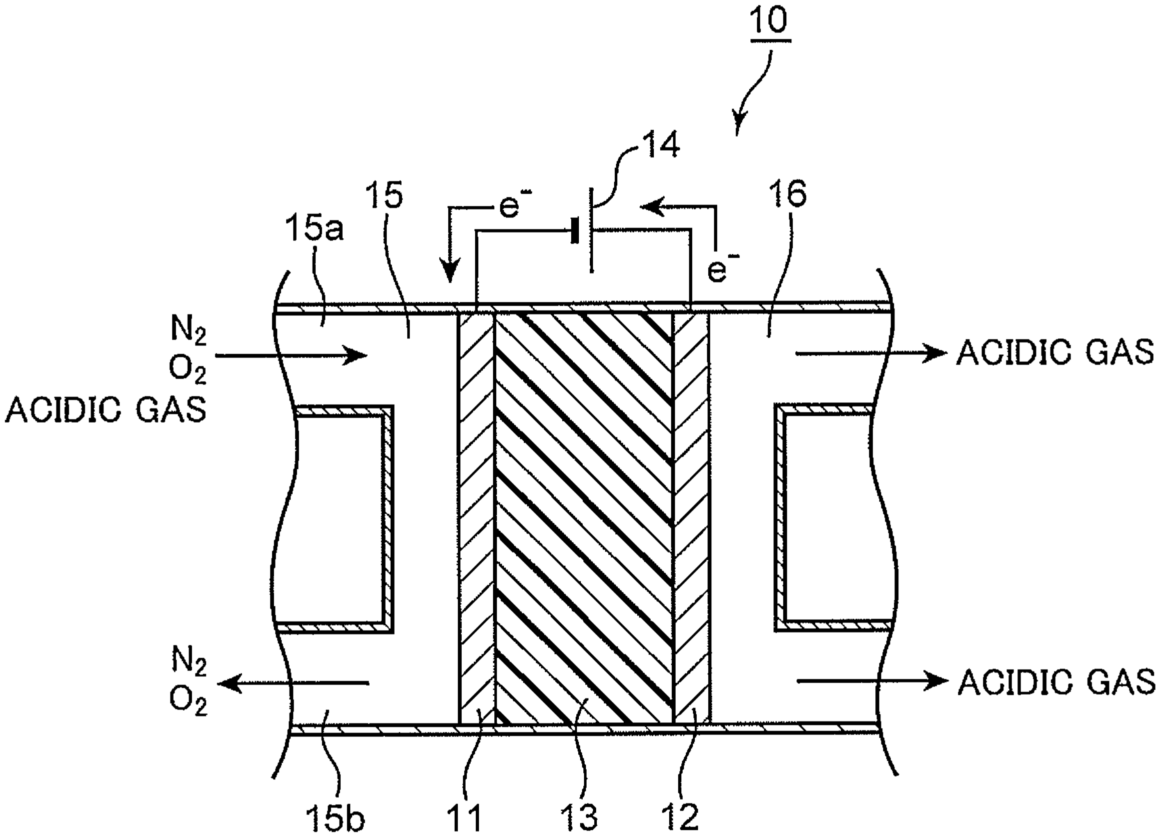
FIG. 1 is a schematic cross-sectional view illustrating a configuration of an acidic gas separation device according to an embodiment of the present invention.

As illustrated in FIG. 1, an acidic gas separation device 10 according to an embodiment of the present invention includes: an electrolyte layer 13; a pair of electrodes 11 and 12 provided with the electrolyte layer 13 interposed therebetween; and a voltage application unit 14 that applies a voltage between the pair of electrodes 11 and 12. The pair of electrodes 11 and 12 are gas permeable electrodes. The electrolyte layer 13 contains: at least one selected from the group consisting of high molecular weight redox compounds having a radicalization rate of 90% or more, high molecular weight redox compounds having a quinone group in the molecule, and high molecular weight redox compounds having an imino group in the molecule; and a nonvolatile electrolytic solution. In addition, it is important that the electrolyte layer 13 contains any of the high molecular weight redox compounds from the viewpoint of long-term repeated durability. Each of the high molecular weight redox compounds is a compound that adsorbs an acidic gas by being subjected to electrolytic reduction and desorbs the adsorbed acidic gas by being subjected to electrolytic oxidation. FIG. 1 is a schematic cross-sectional view illustrating a configuration of the acidic gas separation device 10 according to an embodiment of the present invention.

The term "nonvolatile" means that the substance does not evaporate or does not evaporate immediately under normal temperature and normal pressure, and specifically means that the mass of the substance is maintained at 99 mass % or more even when the substance is left for 24 hours under normal temperature and normal pressure. That is, the nonvolatile electrolytic solution means an electrolytic solution that does not evaporate or does not evaporate immediately under normal temperature and normal pressure, and specifically means an electrolytic solution or the like that retains 99 mass % or more of the mass of the substance even when being left for 24 hours under normal temperature and normal pressure.

In the acidic gas separation device 10 according to the present embodiment, a voltage may be applied by the voltage application unit 14 such that the potential of any one of the pair of electrodes 11 and 12 is higher, and the acidic gas separation device 10 can separate the acidic gas in either case. Here, a case will be described where a voltage is applied between the electrodes 11 and 12 by the voltage application unit 14 such that the potential of one electrode 11 is lower than the potential of the other electrode 12. In this case, the one electrode 11 serves as an electrode (first electrode: cathode electrode) 11 on a side in which the acidic gas is taken in from the gas containing the acidic gas, and the other electrode 12 serves as an electrode (second electrode: anode electrode) 12 on a side in which the acidic gas is released from the electrolyte layer 13.

The acidic gas separation device 10 may include: a first flow path 15 through which gas flows while being in contact with the first electrode 11; and a second flow path 16 through which gas flows while being in contact with the second electrode 12.

The acidic gas separation device 10 according to the present embodiment can easily separate an acidic gas from a gas containing an acidic gas. Specifically, in the acidic gas separation device 10, when a voltage is applied between the electrodes 11 and 12 by the voltage application unit 14 such that the potential of the first electrode 11 is lower than the potential of the second electrode 12, the acidic gas is separated from the gas containing the acidic gas as follows. In the acidic gas separation device 10, when a gas containing an acidic gas, such as air is caused to flow through the first flow path 15, to thereby bring the acidic gas into contact with the first electrode 11, for example, the acidic gas preferentially permeates the electrolyte layer 13 and is released from the second electrode 12 side. Since the acidic gas preferentially permeates the electrolyte layer 13 in this manner, a gas having a high concentration of acidic gas flows through the second flow path 16. As described above, in the acidic gas separation device 10, the acidic gas can preferentially permeate only by applying a voltage between the first electrode 11 and the second electrode 12. Therefore, when the acidic gas separation device 10 is used, the acidic gas is separated from the gas containing the acidic gas. In the acidic gas separation device 10, when a gas containing an acidic gas, nitrogen, and oxygen, for example, air is supplied from a supply port 15*a* of the first flow path 15, the acidic gas (in the case of air, mainly carbon dioxide) is discharged from the second flow path 16, and a gas having a concentration of acidic gas (for example, the concentration of carbon dioxide) lower than that of the supplied gas is discharged from a discharge port 15*b* of the first flow path 15. In addition, the concentration of acidic gas (for example, the concentration of carbon dioxide) has decreased accordingly, a gas having a relatively high concentration of each of nitrogen and oxygen is discharged from the discharge port 15*b* of the first flow path 15.

The above is considered to be due to the following.

The acidic gas, which has come into contact with the first electrode 11 and permeated the first electrode 11, also comes into contact with the electrolyte layer 13. Specifically, the acidic gas contained in the gas present around the first electrode 11 permeates the first electrode 11 and comes into contact with the surface of the electrolyte layer 13 (the surface on the first electrode 11 side). At this time, on the side close to the first electrode 11, the redox compound (high molecular weight redox compound) contained in the electrolyte layer 13 is electrolytically reduced by the voltage applied by the voltage application unit 14, to be a reductant. The acidic gas in contact with the surface of the electrolyte layer 13 (the surface on the first electrode 11 side) is bonded to the reductant and taken in the electrolyte layer 13. Therefore, incorporation of the acidic gas into the first electrode 11 side is promoted. On the other hand, on the side close to the second electrode 12, the high molecular weight redox compound and the reductant of the high molecular weight redox compound contained in the electrolyte layer 13 are electrolytically oxidized by the voltage applied by the voltage application unit 14, to be converted into a radical or an oxidant. Therefore, when the high molecular weight redox compound to which the acidic gas is bonded flows from the side close to the first electrode 11 to the side close to the second electrode 12 in the electrolyte layer 13, the acidic gas bonded to the high molecular weight redox compound is desorbed from the high molecular weight redox compound. That is, even when the acidic gas is bonded to the reductant of the high molecular weight redox compound, the acidic gas is desorbed from the high molecular weight redox compound when the high molecular weight redox compound to which the acidic gas is bonded is electrolytically oxidized on the side close to the second electrode 12. Therefore, when the acidic gas is bonded to the high molecular weight redox compound on the side close to the first electrode 11, and then the high molecular weight redox compound to which the acidic gas is bonded flows to the side close to the second electrode 12 in the electrolyte layer 13, the acidic gas is desorbed from the high molecular weight redox compound on the side close to the second electrode 12. The acidic gas desorbed from the high molecular weight redox compound is then released from the surface of the electrolyte layer 13 (the surface on the second electrode 12 side), and permeates the second electrode 12. It is considered that the acidic gas separation device 10 can take in the acidic gas on the side of first electrode 11 and release the acidic gas on the side of the second electrode, through bonding and desorption of the acidic gas to and from the high molecular weight redox compound as described above.

When a voltage is applied such that the potential of the one electrode 11 is higher than the potential of the other electrode 12, the one electrode 11 becomes an electrode (second electrode) on a side in which the acidic gas is released from the electrolyte layer 13, and the other electrode 12 becomes an electrode (first electrode) 11 on a side in which the acidic gas is taken in from the gas containing the acidic gas. Therefore, the acidic gas can be taken in on the side of the other electrode 12, and the acidic gas can be released on the side of the one electrode 11.

From the above, the acidic gas separation device 10 can continuously separate the acidic gas only by applying a voltage between the pair of electrodes 11 and 12 without inverting the voltage applied between the electrodes (without switching the level of the potential of each electrode). That is, in the acidic gas separation device 10, when a voltage is continuously applied between the pair of electrodes 11 and 12 by the voltage application unit 14, the acidic gas can be continuously separated from the gas containing the acidic gas continuously supplied to the side of the first electrode 11. Therefore, the acidic gas separation device 10 can easily separate the acidic gas from the gas containing the acidic gas.

Meanwhile, when the separation of the acidic gas from the gas containing the acidic gas is continuously performed (continuous operation), the separation of the acidic gas may be inhibited by segregation due to self-aggregation of the redox compound on the surface or inside of the electrolyte layer, the self-aggregation occurring through the diffusion or electrophoresis of the redox compound constituting the electrolyte layer. On the other hand, in the case of the acidic gas separation device 10, use of the redox compound contained in the electrolyte layer 13 as a high molecular weight redox compound promotes entanglement of molecular chains, and thereby suppresses molecular mobility of the redox compound. Therefore, the redox compound becomes difficult to have an aggregation structure, and as a result, segregation of the redox compound in the electrolyte layer can be suppressed. Therefore, the acidic gas separation device 10 can repeatedly perform acidic gas separation over a longer period of time.

The electrolyte layer 13 is not particularly limited as long as it contains: at least one selected from the group consisting of high molecular weight redox compounds having a radicalization rate of 90% or more, high molecular weight redox compounds having a quinone group in the molecule, and high molecular weight redox compounds having an imino group in the molecule; and a nonvolatile electrolytic solution. The electrolyte layer 13 is an acidic gas separator that contributes to separation of an acidic gas.

Here, the high molecular weight redox compound means a redox compound having a repeating unit substantially or conceptually. As the high molecular weight redox compound, specifically, redox compounds which are polymers produced using a monomer as a main component or cross-linked products thereof are exemplified. The high molecular weight redox compound having a radicalization rate of 90% or more is one having a radicalization rate of 90% or more among such high molecular weight redox compounds. In addition, the high molecular weight redox compound having a quinone group in the molecule is one having a quinone group in the molecule among the above-described high molecular weight redox compounds. Examples thereof include high molecular weight redox compounds (polyquinone and the like) obtained by polymerizing a monomer containing a quinone group. In addition, the high molecular weight redox compound having an imino group in the molecule is one having an imino group in the molecule among the above-described high molecular weight redox compounds. Examples thereof include high molecular weight redox compounds (polyaniline and the like) obtained by polymerizing a monomer containing an aniline group.

The high molecular weight redox compound adsorbs and desorbs an acidic gas through electrolytic reduction and electrolytic oxidation. That is, in the high molecular weight redox compound, an acidic gas is adsorbed to the high molecular weight redox compound by electrolytic reduction, and the acidic gas adsorbed to the high molecular weight redox compound is desorbed from the high molecular weight redox compound by electrolytic oxidation.

The weight average molecular weight of the high molecular weight redox compound is not particularly limited, but as the weight average molecular weight of the high molecular weight redox compound is larger, there is a tendency that the high molecular weight redox compound in the electrolyte film can suppress segregation of the redox compound inside or on the surface of the film. Therefore, the lower limit of the weight average molecular weight of the high molecular weight redox compound is preferably 1,000 or more, more preferably 2,000 or more, still more preferably 10,000 or more, and particularly preferably 20,000 or more. On the other hand, by reducing the weight average molecular weight of the high molecular weight redox compound, the solubility of the high molecular weight redox compound is increased, and a sufficient amount of the high molecular weight redox compound can be contained in the electrolyte film. As a result, the separation performance of the acidic gas can be improved. Therefore, the upper limit of the weight average molecular weight of the high molecular weight redox compound is preferably 5,000,000 or less, more preferably 3,000,000 or less, still more preferably 1,000,000 or less, and particularly preferably 500,000 or less. The upper limit of the weight average molecular weight of the high molecular weight redox compound may be 400,000 or less, 300,000 or less, 200,000 or less, 150,000 or less, or 100,000 or less.

Examples of the measurement of the weight average molecular weight of the high molecular weight redox compound herein include a method of performing conversion using standard polymethyl methacrylate by gel permeation chromatography (GPC), and the like.

The high molecular weight redox compound having a radicalization rate of 90% or more is preferably a polymer containing, as a main component of the monomer, a compound having an unpaired electron or a compound having an unpaired electron by oxidation or reduction. The main component means that the proportion of the corresponding component in the monomer is high, and is, for example, preferably 80 mass % or more with respect to the total amount of the monomer.

The high molecular weight redox compound having a radicalization rate of 90% or more is not particularly limited as long as it is a high molecular weight redox compound having a radicalization rate of 90% or more, and examples thereof include poly(N-oxy radical) having a radicalization rate of 90% or more and derivatives thereof. The poly(N-oxy radical) is a high molecular weight redox compound having an N-oxy radical group in the molecule. In this high molecular weight redox compound, when the N-oxy radical group is reduced by, for example, applying a voltage between the electrodes 11 and 12 by the voltage application unit 14, the N-oxy radical group becomes an N-oxy anion group. In addition, when the N-oxy anion group is oxidized by, for example, applying a voltage between the electrodes 11 and 12, the N-oxy anion group returns to the N-oxy radical group.

The high molecular weight redox compound having a quinone group in the molecule is not particularly limited as long as it is a polymer redox compound having a quinone group in the molecule, and examples thereof include polyquinone and derivatives thereof. In the high molecular weight redox compound, when the quinone group is reduced by, for example, applying a voltage between the electrodes 11 and 12 by the voltage application unit 14, the quinone group is becomes a dioxy anion group. In addition, when the dioxy anion group is oxidized by, for example, applying a voltage between the electrodes 11 and 12, the dioxy anion group returns to the quinone group.

The high molecular weight redox compound having an imino group in the molecule is not particularly limited as long as it is a high molecular weight redox compound having an imino group in the molecule, and examples thereof include polyaniline and derivatives thereof. Polyaniline is a linear polymer redox compound in which aniline is bonded at the para position. In this high molecular weight redox compound, when the imino group is reduced by, for example, applying a voltage between the electrodes 11 and 12 by the voltage application unit 14, the imino group becomes an amino anion group. When the amino anion group is oxidized by, for example, applying a voltage between the electrodes 11 and 12, the amino anion group returns to the imino group.

As described above, the high molecular weight redox compound is a compound whose functional group such as an imino group, a quinone group, or an N-oxy radical group is electrochemically changed by oxidation and reduction. Specifically, the high molecular weight redox compound having a radicalization rate of 90% or more is a compound having a functional group interconvertible between a radical group and an anionic group or a cationic group through an oxidation-reduction reaction. The high molecular weight redox compound is preferably a polymer containing, as a constituent unit thereof, a monomer unit whose functional group portion thereof has a functional group interconvertible between a radical group and an anionic group or a cationic group through an oxidation-reduction reaction. The polymer may be obtained by polymerizing a monomer having a functional group interconvertible between a radical group and an anionic group or a cationic group through an oxidation-reduction reaction, or may be obtained by introducing a functional group interconvertible between a radical group and an anionic group or a cationic group through an oxidation-reduction reaction into a part or all of the monomer units of the polymer by post-modification. The high molecular weight redox compound may be crosslinked.

The amount of the monomer unit having a functional group interconvertible between a radical group and an anionic group or a cationic group through an oxidation-reduction reaction is preferably 80 mol % or more, more preferably 90 mol % or more, and still more preferably 95 mol % or more, with respect to the amounts of all monomer units constituting the polymer (polymer containing, as a constituent unit thereof, a monomer unit having a functional group interconvertible between a radical group and an anionic group or a cationic group through an oxidation-reduction reaction). Within the above range, it is preferable in terms of retention and transport efficiency of the acidic substance.

Examples of the monomer unit constituting the high molecular weight redox compound having a radicalization rate of 90% or more include monomer units in a case of polymerizing, as a monomer, at least one selected from 4-acryloyloxy-2,2,6,6-tetramethylpiperidinyloxy radical, 4-methacryloyloxy-2,2,6,6-tetramethylpiperidinyloxy radical, 3-acryloyloxy-2,2,6,6-tetramethylpyrrolidinyloxy radical, 3-methacryloyloxy-2,2,6,6-tetramethylpyrrolidinyloxy radical, 4-vinyloxy-2,2,6,6-tetramethylpiperidinyloxy radical, or 4-vinyloxy-2,2,5,5-tetramethylpyrrolidinyloxy radical. That is, examples of the high molecular weight redox compound having a radicalization rate of 90% or more include polymers obtained by polymerizing these compounds as monomers.

Examples of the monomer unit constituting the high molecular weight redox compound having a quinone group in the molecule include monomer units in a case of polymerizing, as a monomer, at least one selected from 2-vinyl-1,4-benzoquinone, 2-vinyl-1,4-naphthoquinone, 2,5-diacryloyloxymethyl-1,4-benzoquinone, 2,6-diacryloyloxymethyl-1,4-naphthoquinone, 1,4-diacryloyloxymethyl anthraquinone, 1,4-diacryloyloxyethyl naphthoquinone, 1,4-dichloroanthraquinone, 1,4-dibromoanthraquinone, 1,4-dichloronaphthoquinone, 1,4-dibromonaphthoquinone, 2,5-dichlorobenzoquinone, or 2,5-dibromobenzoquinone. That is, examples of the high molecular weight redox compound having a quinone group in the molecule include polymers obtained by polymerizing these compounds as monomers.

Examples of the monomer unit constituting the high molecular weight redox compound having an imino group in the molecule include monomer units in a case of polymerizing, as a monomer, at least one selected from aniline, 1,4-diaminonaphthalene, 2-methyl-aniline, 2,3-dimethylaniline, 1,4-diaminonaphthalene, or 9,10-diaminoanthracene. That is, examples of the high molecular weight redox compound having an imino group in the molecule include polymers obtained by polymerizing these compounds as monomers.

The polymer compound may contain only one type or two or more types of the monomer units. That is, the polymer compound may be a polymer obtained by polymerizing a monomer alone, or may be a polymer obtained by polymerizing two or more types of monomers in combination. In addition, the high molecular weight redox compound may be a compound obtained by polymerizing only the above-described monomer, or may be a copolymer obtained by copolymerizing the above-described monomer with a copolymerizable monomer such as ethylene, propylene, butadiene, isoprene, styrene, or vinyl acetate. The copolymerizable monomer may be used alone or in combination of two or more types thereof.

Among the compounds exemplified above, the high molecular weight redox compound is preferably a high molecular weight redox compound having a radicalization rate of 90% or more, and more preferably a compound containing a repeating unit represented by the following formula (1) from the viewpoint of electrochemical stability. The compound containing a repeating unit represented by the following formula (1) may contain a single repeating unit, or two or more types thereof may be used in combination.

[Chemical Formula 1]

(1)

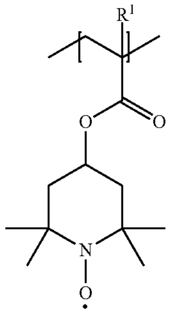

In the formula (1), $R^1$ represents a hydrogen atom or a methyl group.

The compound containing the repeating unit represented by the formula (1) may be a compound obtained by synthesis by a predetermined synthesis method, or may be a commercially available product. The synthesis method is not particularly limited as long as it is a synthesis method by which a compound containing the repeating unit represented by the formula (1) is obtained. Examples of the synthesis method include a method in which the amino group of the disubstituted amine compound is oxidized to nitroxide, and the like.

The radicalization rate of the high molecular weight redox compound having a radicalization rate of 90% or more is not particularly limited as long as it is 90% or more, and is, for example, preferably 90 to 99 mass %, more preferably 95 to 99 mass %, and still more preferably 97 to 99 mass %. When the radicalization rate is too low, reactivity with an acidic gas such as carbon dioxide tends to decrease, leading to a decrease in transport efficiency. The radicalization rate is a proportion of monomer units whose functional group are a radical group in all monomer units (total monomer units having a functional group interconvertible between a radical group and an anionic group or a cationic group through an oxidation-reduction reaction) in the case of a polymer containing, as a constituent unit thereof, a monomer unit having a functional group interconvertible between a radical group and an anionic group or a cationic group through an oxidation-reduction reaction. In the case of a compound containing a repeating unit represented by the formula (1), the radicalization rate is the content of the repeating unit represented by the formula (1) with respect to the amount of all monomer units.

Examples of the method for measuring the radicalization rate (the content of the repeating unit represented by the formula (1)) include methods calculating by a method in which a nitroxide free group is quantified using, for example, a chemical titration method (oxidation-reduction titration method) based on oxidation-reduction reaction, a method in which a spin concentration in a reaction product is quantified by electron spin resonance (ESR), or the like.

The electrolyte layer 13 contains a nonvolatile electrolytic solution. The electrolytic solution is preferably an electrochemically stable compound having a wide potential window. The electrolytic solution is not particularly limited as long as it is nonvolatile and can be used as an electrolytic solution. As the electrolytic solution, an ionic liquid is preferably used. When the ionic liquid is used as the electrolytic solution, the ionic liquid can have both functions of an electrolyte and a solvent without containing the electrolyte and the solvent. In addition, as described above, the electrolytic solution may be any liquid that is nonvolatile and can be used as the electrolytic solution, and may be a liquid in which an electrolyte is contained in an ionic liquid, a liquid in which a solvent is contained in an ionic liquid, a liquid in which an electrolyte and a solvent are contained in an ionic liquid, or a liquid composed of an ionic liquid. Among them, the electrolytic solution is preferably a liquid composed of an ionic liquid, that is, the electrolytic solution is preferably an ionic liquid. In addition, it is preferable to use an ionic liquid as the electrolytic solution from the viewpoint that the ionic liquid hardly volatilizes and has high flame retardancy. The ionic liquid has relatively high ion conductivity. From these viewpoints, when the ionic liquid is used as the electrolytic solution, separation of the acidic gas from the gas containing the acidic gas can be performed more safely and continuously for a longer time by the acidic gas separation device.

The ionic liquid is not particularly limited as long as it is a known ionic liquid, and examples thereof include an imidazolium-based ionic liquid, a pyridine-based ionic liquid, an alicyclic amine-based ionic liquid, and an azonium amine-based ionic liquid.

Examples of the ionic liquid include 1-ethyl-3-methylimidazolium bis(fluorosulfonyl)imide, 1-methyl-3-octylimidazolium tetrafluoroborate, 1-ethyl-3-methylimidazolium tetrafluoroborate, 1-butyl-3-methylimidazolium chloride, 1-butyl-3-methylimidazolium tetrafluoroborate, 1-butyl-3-methylimidazolium bis(trifluoromethylsulfonylimide), 1-decyl-3-methylimidazolium tetrafluoroborate, 1,3-dimethylimidazolium tetrafluoroborate, 1,3-diethoxyimidazolium tetrafluoroborate, 1-methyl-3-octylimidazolium hexafluorophosphate, 1-ethyl-3-methylimidazolium hexafluorophosphate, and 1-butyl-3-methylimidazolium hexafluorophosphate, 1-decyl-3-methylimidazolium hexafluorophosphate, 1,3-dimethoxyimidazolium hexafluorophosphate, and 1,3-diethoxyimidazolium hexafluorophosphate. Among the ionic liquids exemplified above, the ionic liquid is preferably 1-ethyl-3-methylimidazolium bis(fluorosulfonyl)imide, 1-methyl-3-octylimidazolium tetrafluoroborate, 1-ethyl-3-methylimidazolium tetrafluoroborate, 1-butyl-3-methylimidazolium tetrafluoroborate, 1-butyl-3-methylimidazolium bis(trifluoromethylsulfonylimide), 1-butyl-3-methylimidazolium chloride, 1,3-dimethylimidazolium tetrafluoroborate, 1-methyl-3-octylimidazolium hexafluorophosphate, and 1-ethyl-3-methylimidazolium hexafluorophosphate. In addition, as the ionic liquid, 1-ethyl-3-methylimidazolium bis(fluorosulfonyl)imide, 1-methyl-3-octylimidazolium tetrafluoroborate, 1,3-dimethoxyimidazolium tetrafluoroborate, 1-butyl-3-methylimidazolium bis(trifluoromethylsulfonylimide), 1-butyl-3-methylimidazolium chloride, and 1-methyl-3-octylimidazolium hexafluorophosphate are more preferable, and 1-ethyl-3-methylimidazolium bis(fluorosulfonyl)imide, 1-butyl-3-methylimidazolium bis(trifluoromethylsulfonylimide), 1-butyl-3-methylimidazolium chloride, and 1-methyl-3-octylimidazolium tetrafluoroborate are still more preferable.

As described above, the electrolytic solution is not particularly limited as long as it is nonvolatile and can be used as an electrolytic solution, and examples thereof include electrolytic solutions containing an electrolyte and a solvent, in addition to the ionic liquid.

The solvent is not particularly limited as long as it is nonvolatile and can be used as a solvent of the electrolytic solution. The solvent is required to be nonvolatile, and preferably has a boiling point of 200° C. or higher, for example. Examples of the solvent include polyethers. Examples of the polyether include polyethylene glycol, polypropylene glycol, and polytetramethylene ether glycol. The polyether may be a homopolymer of these compound or a copolymer of these compounds. Examples of the polyethylene glycol, polypropylene glycol, polytetramethylene ether glycol, and copolymers thereof include those obtained by performing ring-opening polymerization using monomers such as ethylene oxide, propylene oxide, and tetrahydrofuran alone or in combination of two or more types thereof. The polyether preferably has a low molecular weight from the viewpoint of fluidity, and specifically preferably has a weight average molecular weight of about 200 to 500. The solvent may be used alone or in combination of two or more types thereof.

The electrolyte is not particularly limited, and examples thereof include quaternary ammonium salts, inorganic salts, and hydroxides. Examples of the quaternary ammonium salt include tetramethylammonium tetrafluoroborate, tetra-n-ethylammonium tetrafluoroborate, tetra-n-propylammonium tetrafluoroborate, tetra-n-butylammonium tetrafluoroborate, n-hexadecyltrimethylammonium tetrafluoroborate, tetra-n-hexadecylammonium tetrafluoroborate, tetra-n-octylammonium tetrafluoroborate, tetra-n-ethylammonium perchlorate, tetra-n-butylammonium perchlorate, and tetraoctadecylammonium perchlorate. Examples of the inorganic salt include lithium perchlorate, sodium perchlorate, potassium perchlorate, sodium acetate, potassium acetate, sodium nitrate, and potassium nitrate. Examples of the hydroxide include sodium hydroxide and potassium hydroxide. Among the electrolytes exemplified above, the electrolyte is preferably tetramethylammonium tetrafluoroborate, tetra-n-ethylammonium tetrafluoroborate, tetra-n-propylammonium tetrafluoroborate, tetra-n-butylammonium tetrafluoroborate, n-hexadecyltrimethylammonium tetrafluoroborate, tetra-n-hexadecylammonium tetrafluoroborate, tetra-n-octylammonium tetrafluoroborate, tetra-n-ethylammonium perchlorate, tetra-n-butylammonium perchlorate, tetraoctadecylammonium perchlorate, lithium perchlorate, sodium perchlorate, sodium acetate, or potassium acetate. Among them, as the electrolyte, tetra-n-ethylammonium tetrafluoroborate, tetra-n-propylammonium tetrafluoroborate, tetra-n-butylammonium tetrafluoroborate, lithium perchlorate, and sodium perchlorate are more preferable, and tetra-n-butylammonium tetrafluoroborate and lithium perchlorate are still more preferable. In addition, the electrolyte may stabilize carbonate ions or bicarbonate ions as a supporting salt thereof and have pH buffering ability. As the electrolyte in this case, specifically, sodium bicarbonate, sodium carbonate, acetic acid, and sodium acetate are exemplified. As the electrolyte, the above-exemplified electrolyte may be used alone, or two or more types thereof may be used in combination.

The electrolytic solution preferably hardly dissolves an acidic gas. In the acidic gas separation device according to the present embodiment, the acidic gas is taken in the electrolyte layer 13 by bonding of the acidic gas to the reductant of the high molecular weight redox compound. Therefore, even when the electrolytic solution hardly dissolves the acidic gas, the acidic gas is bonded to the reductant of the high molecular weight redox compound on the surface of the electrolyte layer 13, and the acidic gas can be taken in the electrolyte layer 13. In addition, in the case of using such an electrolytic solution that hardly dissolves the acidic gas, when the acidic gas is released from the electrolyte layer 13, the acidic gas is hardly dissolved in the electrolytic solution, so that the acidic gas is easily released. Therefore, the acidic gas separation device according to the present embodiment can more easily separate the acidic gas from the gas containing the acidic gas.

In the electrolyte layer 13, the electrolytic solution may be gelled. When such an electrolyte layer made of a gel is used, liquid leakage of the electrolytic solution constituting the electrolyte layer 13 can be suppressed. Even when the electrolyte layer 13 is a gel containing an electrolytic solution and the high molecular weight redox compound, as described above, an acidic gas can be taken in on the first electrode side, and the acidic gas can be released on the second electrode side. Therefore, it is possible to suppress inhibition of separation of the acidic gas from the gas containing the acidic gas due to liquid leakage of the electrolytic solution or the like, and to continuously perform the separation for a longer time. In order to obtain an electrolyte layer made of a gel as described above, for example, a gelling agent for gelling may be added to the electrolytic solution, a gelling electrolyte or a polymer electrolyte may be used, or the high molecular weight redox compound may be gelled. In addition, an inorganic oxide such as silica gel, alumina, titania, or zirconia may be added to the electrolyte layer. The gel can be strengthened by adding the inorganic oxide. For example, the gelling agent can be combined with the inorganic oxide to form a stronger gel. Examples of the gelling agent include a polymer, a gelling agent utilizing a technique such as a polymer cross-linking reaction, a polymerizable polyfunctional monomer, and an oil gelling agent. The gelling electrolyte and the polymer electrolyte are not particularly limited as long as they can be used as a gelling electrolyte or a polymer electrolyte. Examples thereof include vinylidene fluoride-based polymers such as polyvinylidene fluoride; acrylic acid-based polymers such as polyacrylic acid; acrylonitrile-based polymers such as polyacrylonitrile; polyether-based polymers such as polyethylene oxide; and compounds having an amide structure in the structure thereof.

The electrolyte layer 13 may contain components other than the electrolytic solution and the high molecular weight redox compound (other components). Examples of the other components include polyethylene glycol, polyacrylate, polymethacrylate, and polyvinyl alcohol acetal.

The electrolyte layer 13 may or may not include a substrate (support), but preferably includes a substrate (support). Examples of the electrolyte layer 13 include those obtained by impregnating a substrate (support) with the electrolytic solution containing the high molecular weight redox compound. In addition, as the substrate (support), for example, a paper-like material and a nonwoven fabric are preferable, and a nonwoven fabric is more preferable, from the viewpoint of avoiding complexity in the production process, maintaining strength, and maintaining flexibility. Fibers constituting the nonwoven fabric are not particularly limited, and examples thereof include polyolefin-based fibers; cellulose-based fibers; (meth)acrylic-based fibers; polyvinyl alcohol-based fibers; polyvinyl chloride-based fibers; polystyrene-based fibers; polyester-based fibers such as polyethylene terephthalate fibers, polybutylene terephthalate fibers, polytrimethylene terephthalate fibers, and molten liquid crystal-forming wholly aromatic polyester fibers; polyamide-based fibers; polycarbonate-based fibers; and polyurethane-based fibers. As the fibers constituting the nonwoven fabric, one selected from these fibers may be used, or two or more types thereof may be used in combination. Among these fibers, those containing polyester-based fibers or polyvinyl alcohol-based fibers can be preferably adopted from the viewpoint of expressing the strength of the substrate (support) or the strength of the entire electrolyte layer. The polyvinyl alcohol-based fibers may be one that have been modified, and examples thereof include polyvinyl alcohol fibers and ethylene-modified polyvinyl alcohol fibers. When the polyester-based fibers are contained, molten liquid crystal-forming wholly aromatic polyester fibers can be particularly preferably adopted among the above examples.

Examples of the type of the nonwoven fabric include nonwoven fabrics formed by a wet process or a dry process, meltblown nonwoven fabrics, spunlace nonwoven fabrics, thermal bond nonwoven fabrics, and nonwoven fabrics formed by a needle punch method. Among these nonwoven fabrics, nonwoven fabrics made of long fibers are preferably used, and meltblown nonwoven fabrics are preferable. The production method of the paper-like material is not particularly limited, and those produced by a method such as wet papermaking can also be used.

The degree of gas permeability and the film thickness of the substrate (support) can be set by controlling the basis weight. The basis weight of the substrate (support) is preferably 50 $g/m^2$ or less, more preferably 45 $g/m^2$ or less, and still more preferably 40 $g/m^2$ or less, because a smaller basis weight of the substrate (support) increases the degree of gas permeability, so that components constituting the electrolyte layer, such as a high molecular weight redox compound can be preferably loaded in the substrate (support). The basis weight of the substrate (support) may be 35 $g/m^2$ or less, 30 $g/m^2$ or less, 25 $g/m^2$ or less, or 20 $g/m^2$ or less. In addition, the basis weight of the substrate (support) is preferably larger from the viewpoint of the mechanical strength of the electrolyte layer. The basis weight of the substrate (support) is preferably 1 $g/m^2$ or more, more preferably 2 $g/m^2$ or more, and still more preferably 3 $g/m^2$ or more. The basis weight of the substrate (support) may be 5 $g/m^2$ or more, 7 $g/m^2$ or more, or 10 $g/m^2$ or more.

The thickness of the substrate (support) is not particularly limited, but in order to adjust the thickness of the electrolyte layer 13, the thickness of the substrate (support) is equal to or less than the thickness of the electrolyte layer 13. The thickness of the substrate (support) is usually preferably 1 μm or more, more preferably 5 μm or more, still more preferably 6 μm or more, and particularly preferably 7 μm or more. The thickness of the substrate (support) is preferably 1,000 μm or less, more preferably 800 μm or less, and still more preferably 600 μm or less. The thickness of the substrate (support) may be 500 μm or less, 400 μm or less, 300 μm or less, 200 μm or less, 100 μm or less, 50 μm or less, or 30 μm or less.

The method for producing the electrolyte layer 13 is not particularly limited. In a case where the electrolyte layer 13 includes the substrate (support), for example, a method is exemplified in which a high molecular weight redox compound is dispersed and dissolved in an electrolytic solution and a substrate (support) is impregnated with the electrolytic solution containing the high molecular weight redox compound. The impregnation is preferably performed while ultrasonic vibration is applied to the electrolytic solution or the substrate (support). By performing such impregnation, formation of minute holes, that is, formation of pinholes in the electrolyte layer can be suppressed.

The thickness of the electrolyte layer 13 is not particularly limited as long as it is a thickness that does not cause breakage due to passage of gas, pinholes, cracks, and the like. The thickness of the electrolyte layer 13 is, for example, preferably 1 μm or more, more preferably 5 μm or more, still more preferably 6 μm or more, and particularly preferably 7 μm or more. The thickness of the electrolyte layer 13 is, for example, preferably 1,000 μm or less, more preferably 800 μm or less, and still more preferably 600 μm or less. The thickness of the electrolyte layer 13 may be 550 μm or less, 500 μm or less, 450 μm or less, 400 μm or less, 350 μm or less, 250 μm or less, 150 μm or less, 100 μm or less, 80 μm or less, 40 μm or less, or 30 μm or less. When the thickness of the electrolyte layer 13 is the above lower limit or more, complication in the production process of the acidic gas separation device can be suppressed. When the thickness of the electrolyte layer 13 is the above upper limit or less, it is easy to reduce the voltage (voltage to be applied between the pair of electrodes in order to separate the acidic gas) used for transporting the acidic gas.

The difference between the thickness of the electrolyte layer 13 and the thickness of the support (the difference obtained by subtracting the thickness of the support from the thickness of the electrolyte layer 13: the thickness of the electrolyte layer—the thickness of the support) is not particularly limited, and may be 0 μm. However, when the difference is larger than 0 μm, the adhesion between the electrode and the electrolyte layer is improved, and as a result, the transport efficiency of the acidic gas can be increased. The difference obtained by subtracting the thickness of the support from the thickness of the electrolyte layer 13 is preferably 1 μm or more and 500 μm or less. With the electrolyte layer having such a difference, the transport efficiency of the acidic gas can be increased, and the acidic gas can be more suitably separated from the gas containing the acidic gas.

The ratio of the thickness of the support to the thickness of the electrolyte layer 13 (thickness of support/thickness of electrolyte layer) is not particularly limited. The ratio of the thickness of the support to the thickness of the electrolyte layer 13 is preferably 1 or less and preferably 0.99 or less from the viewpoint of improving adhesion between the electrolyte layer and the electrode. In addition, the ratio of the thickness of the support to the thickness of the electrolyte layer 13 is preferably 0.3 or more, and preferably 0.4 or more from the viewpoint of achieving both the maintenance of the strength of the electrolyte layer and the separation.

Next, a pair of electrodes (electrodes 11 and 12), which are one of the constituents of the acidic gas separation device according to the present embodiment, will be described.

The pair of electrodes 11 and 12 are not particularly limited as long as they are gas permeable electrodes. That is, the electrodes 11 and 12 are only required to be any conductive member that allows a gas such as carbon dioxide to permeate and allows a current to flow through the electrolyte layer 13 sandwiched between the pair of electrodes 11 and 12. In addition, as the electrodes 11 and 12, a porous body having conductivity to such an extent that movement of electrons is not hindered and excellent gas permeability is preferable, and specifically, an electrode made of a porous conductive material, and the like are exemplified. As the electrodes 11 and 12, more specifically, a porous body containing carbon as a main component, a porous body made of carbon, a porous metal layer, and the like are exemplified. Examples of the porous conductive material include a porous metal, a porous body containing carbon as a main component, and a porous body made of carbon. As the porous conductive material, these may be used alone or in combination of two or more types thereof. That is, the pair of electrodes 11 and 12 may be electrodes made of a single conductive material among these porous conductive materials, or may be electrodes formed by combining two or more conductive materials.

The porous metal layer is a metal layer having a large number of pores formed therein. In addition, in the metal layer, the pores are preferably formed over the entire metal layer from the viewpoint of excellent gas permeability. The method for obtaining the porous metal layer is not particularly limited as long as it is a method of applying a treatment for forming a large number of pores to a metal layer in which a large number of pores are not formed (a method for forming pores). Examples of the method include physical methods such as cutting, polishing, and sandblasting, and chemical methods such as electrolytic etching and electroless etching using an etching solution such as an acid or a base. In addition, as a method for forming pores, each of the above-described methods may be performed alone, two or more thereof may be performed in combination. In addition, as the method for forming pores, a chemical method is preferable in order to form pores (fine pores) more densely, from the viewpoint of increasing the surface area. The material of the metal layer is not particularly limited, and examples thereof include aluminum, copper, silver, gold, iron, titanium, molybdenum, tungsten, nickel, and alloys thereof. Examples of the alloy include stainless steel, and the like. Among them, copper, silver, titanium, SUS316, and SUS321 are preferably used as the material of the metal layer from the viewpoint of durability and processability.

As the carbon contained in the porous body, specifically, carbonaceous materials such as graphite, carbon nanotubes, activated carbon, activated carbon fiber, carbon fibers, and the like are exemplified. The carbon is preferably activated carbon or activated carbon fiber from the viewpoint of corrosion resistance and specific surface area. As the carbon, various carbonaceous materials may be used alone or in combination of two or more types thereof. As the porous body containing carbon, a porous body obtained by forming a carbonaceous material into a cloth shape or a felt shape is preferable. Therefore, as the electrode as a porous body, specifically, a carbon sheet, a carbon cloth, carbon paper, and the like are exemplified. Other examples of the electrode as a porous body include: a carbon-based electrode containing activated carbon or carbon fiber; and an electrode containing a needle-shaped conductive material and having a high porosity.

The pair of electrodes 11 and 12 are preferably an electrode containing at least one selected from the group consisting of porous metal, graphite, carbon nanotubes, and carbon fiber among the above-described electrodes. With such an electrode, it is considered that the gas can suitably permeate the electrodes, and a voltage can be suitably applied between the electrodes 11 and 12 by the voltage application unit 14. Therefore, by using this electrode, an acidic gas separation device capable of more suitably separating an acidic gas from a gas containing an acidic gas is obtained.

When the porous body constituting the pair of electrodes 11 and 12 is a particulate material, the porous body can be formed into an electrode by forming the particulate material into a sheet shape using a binder, or can be formed by forming a film of the particulate material on a mesh having conductivity. The binder that can be used is not particularly limited, and examples thereof include: a mixture of polyvinylidene fluoride (PVDF), polytetrafluoroethylene, and styrene-butadiene rubber (SBR) with carboxymethyl cellulose (CMC); a copolymer of polyacrylic acid, acrylic acid, and acrylonitrile; and polyvinyl alcohol and partially modified products thereof.

When a film of the particulate material of the porous body is formed on the mesh-like conductor, as a mesh that can be used, a mesh made of a thin wire of iron, nickel, stainless steel, or the like, expanded metal obtained from a metal foil, paper made of synthetic fiber or natural fiber, or a nonwoven fabric subjected to conductive plating can be used.

The thickness of the mesh is not particularly limited, but in order to adjust the thicknesses of the electrodes 11 and 12, the thickness of the mesh is equal to or less than the thicknesses of the electrodes 11 and 12, and is usually preferably 5 μm to 1 mm, preferably 6 μm to 800 μm, and more preferably 7 μm to 600 μm.

The BET specific surface areas of the electrodes 11 and 12 are not particularly limited, but are, for example, preferably 1 $m^2/g$ or more, more preferably 100 $m^2/g$ or more, and still more preferably 500 $m^2/g$ or more. The BET specific surface areas of the electrodes 11 and 12 are preferably large from the viewpoint of permeability of gas (gas permeability), but are preferably 3,000 $m^2/g$ or less from the relationship of the strength and the like of the electrodes 11 and 12. Therefore, the BET specific surface areas of the electrodes 11 and 12 are preferably 1 to 3,000 $m^2/g$, more preferably 100 to 2,500 $m^2/g$, and still more preferably 500 to 2,000 $m^2/g$. When the BET specific surface areas of the electrodes are too small, the permeability of gas (gas permeability) is reduced, and permeation of carbon dioxide tends to be inhibited. When the BET specific surface areas of the electrodes are too large, the strength and the like of the electrodes tend to be insufficient. From these respects, when the BET specific surface area of the electrode is within the above range, the separation of carbon dioxide can be repeatedly realized over a long period of time. The BET specific surface area is a specific surface area measured by a BET method, and can be measured by a known method. Examples of the method for measuring the BET specific surface area include a method of performing nitrogen adsorption isotherm measurement and calculating the BET specific surface area from the obtained adsorption isotherm, and the like.

As described above, the electrodes 11 and 12 are conductive members capable of causing a current to flow through the electrolyte layer 13 sandwiched between the pair of electrodes 11 and 12. The surface resistance values of the electrodes 11 and 12 are preferably as small as possible, and is, for example, preferably 1 kΩ/sq or less, and more preferably 200 Ω/sq or less. The surface resistance values of the electrodes are preferably as small as possible, but is actually limited to 1 Ω/sq. Therefore, the surface resistance values of the electrodes are preferably 1 Ω/sq to 1 kΩ/sq, and more preferably 10 to 200 Ω/sq. With an electrode having such a surface resistance value, a current can suitably flows through the electrolyte layer 13, and carbon dioxide can be suitably separated.

The thicknesses of the electrodes 11 and 12 are not particularly limited, but are preferably a thickness that allows adsorption of carbon dioxide and suitable prevention of liquid leakage of the electrolytic solution. The thicknesses of the electrodes 11 and 12 are, for example, preferably 20 μm or more and 10 mm or less, and more preferably 50 μm or more and 5 mm or less. When each of the electrodes is too thin, the strength and the like of the electrodes tend to be insufficient. In addition, when the electrodes are too thick, the permeability of gas (gas permeability) is reduced, and permeation of carbon dioxide tends to be inhibited. From these respects, when the thickness of the electrode is within the above range, the separation of carbon dioxide can be repeatedly realized over a long period of time.

In addition, the voltage application unit 14 is not particularly limited as long as a voltage can be applied between the pair of electrodes 11 and 12. That is, as described above, the voltage application unit 14 applies a voltage between the pair of electrodes 11 and 12 such that the potential of any one of the pair of electrodes 11 and 12 is higher. In addition, preferably, the voltage application unit 14 applies a voltage such that the potential of the first electrode on a side in which the acidic gas is taken in from the gas containing the acidic gas is always lower than the potential of the second electrode on a side in which the acidic gas is released from the electrolyte layer. By doing so, it is possible to take in the acidic gas on the first electrode side and release the acidic gas on the second electrode side only by applying a voltage by the voltage application unit such that the potential of the first electrode is always lower than the potential of the second electrode. In addition, the voltage application unit 14 may be an application unit that cannot invert the voltage applied between the electrodes, and examples thereof include a secondary battery, an external power supply, and a capacitor.

The first flow path 15 and the second flow path 16 are not particularly limited as long as they are flow paths through which gas can flow.

The method for producing the acidic gas separation device 10 according to the present embodiment is not particularly limited as long as the device having the above structure can be produced. Specifically, exemplified is a method of assembling the pair of electrodes 11 and 12, the electrolyte layer 13, the voltage application unit 14, the first flow path 15, and the second flow path 16, by a general assembling method so as to have the structure illustrated in FIG. 1.

Examples of the acidic gas include carbon dioxide, NOx (nitrogen oxide), SOx (sulfur oxide), and hydrogen sulfide. The acidic gas may contain one type of acidic gas or two or more types of acidic gases.

The installation place of the acidic gas separation device according to the present embodiment is not particularly limited as long as it is a place where separation of an acidic gas is required. The apparatus may be used as an apparatus including the acidic gas separation device. Examples of the apparatus including the acidic gas separation device include an air purifier, an air conditioner, and an acidic gas concentration apparatus. More specifically, an acidic gas concentration apparatus for separating and concentrating an acidic gas in the air is exemplified, and the apparatus can be used, for example, for agriculture and the like. Examples of the apparatus including the acidic gas separation device for separating and removing an acidic gas in a room include an air purifier and an air conditioner. These can be used to adjust the concentration of acidic gas in private cars, buses, trains, airplanes, space stations, and the like.

Figure 2:
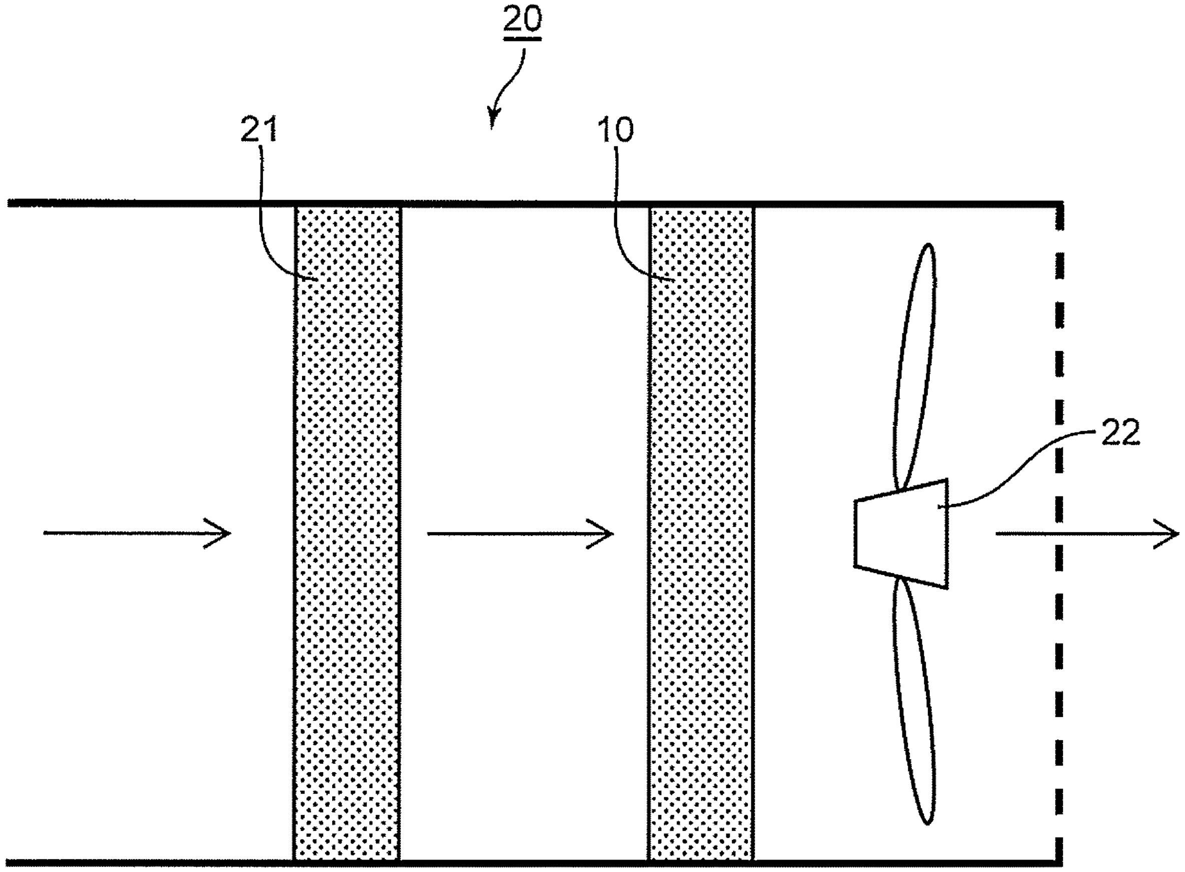
FIG. 2 is a schematic view illustrating a configuration of an air purifier including the acidic gas separation device according to an embodiment of the present invention.

An air purifier according to another embodiment of the present invention is an air purifier including the acidic gas separation device. Examples of the air purifier according to the present embodiment include an air purifier 20 illustrated in FIG. 2, and the like. The air purifier 20 includes a dust collecting/deodorizing filter 21, the acidic gas separation device 10, and a fan 22. The dust collecting/deodorizing filter 21 is not particularly limited as long as it can perform a dust collecting treatment for removing house dust and the like from a gas and a deodorizing treatment for deodorizing the gas by causing a supplied gas such as air to pass through the dust collecting/deodorizing filter 21. Examples thereof include a dust collecting/deodorizing filter provided in a general air purifier, and the like. The fan 22 is not particularly limited as long as the gas from which the acidic gas has been removed by the acidic gas separation device 10 can flow to a place where the air purifier 20 is installed, such as a room. The air purifier 20 supplies the air subjected to the dust collecting treatment and the deodorizing treatment by the dust collecting/deodorizing filter 21 to the acidic gas separation device 10, separates the acidic gas by the acidic gas separation device 10, and causes the gas from which the acidic gas has been separated to flow to a place where the air purifier 20 is installed, such as a room by the fan 22. As a result, the air purifier 20 can supply the air, which has been subjected to the dust collecting treatment and the deodorizing treatment and whose concentration of acidic gas has been reduced, to a place where the air purifier 20 is installed, such as a room. That is, the air purifier 20 can separate the acidic gas by the acidic gas separation device 10, and can reduce the concentration of acidic gas contained in the gas such as air supplied from the air purifier 20 by removing the separated acidic gas. The air purifier according to the present embodiment is not particularly limited as long as the air purifier includes the acidic gas separation device, and is not limited to the air purifier that supplies gas such as air subjected to a dust collecting treatment and a deodorizing treatment by the dust collecting/deodorizing filter 21 to the acidic gas separation device 10 as described above. The air purifier according to the present embodiment may be, for example, an air purifier that supplies a gas from which an acidic gas has been removed by the acidic gas separation device to the dust collecting/deodorizing filter, and performs a dust collecting treatment and a deodorizing treatment on the gas by the dust collecting/deodorizing filter.

Figure 3:
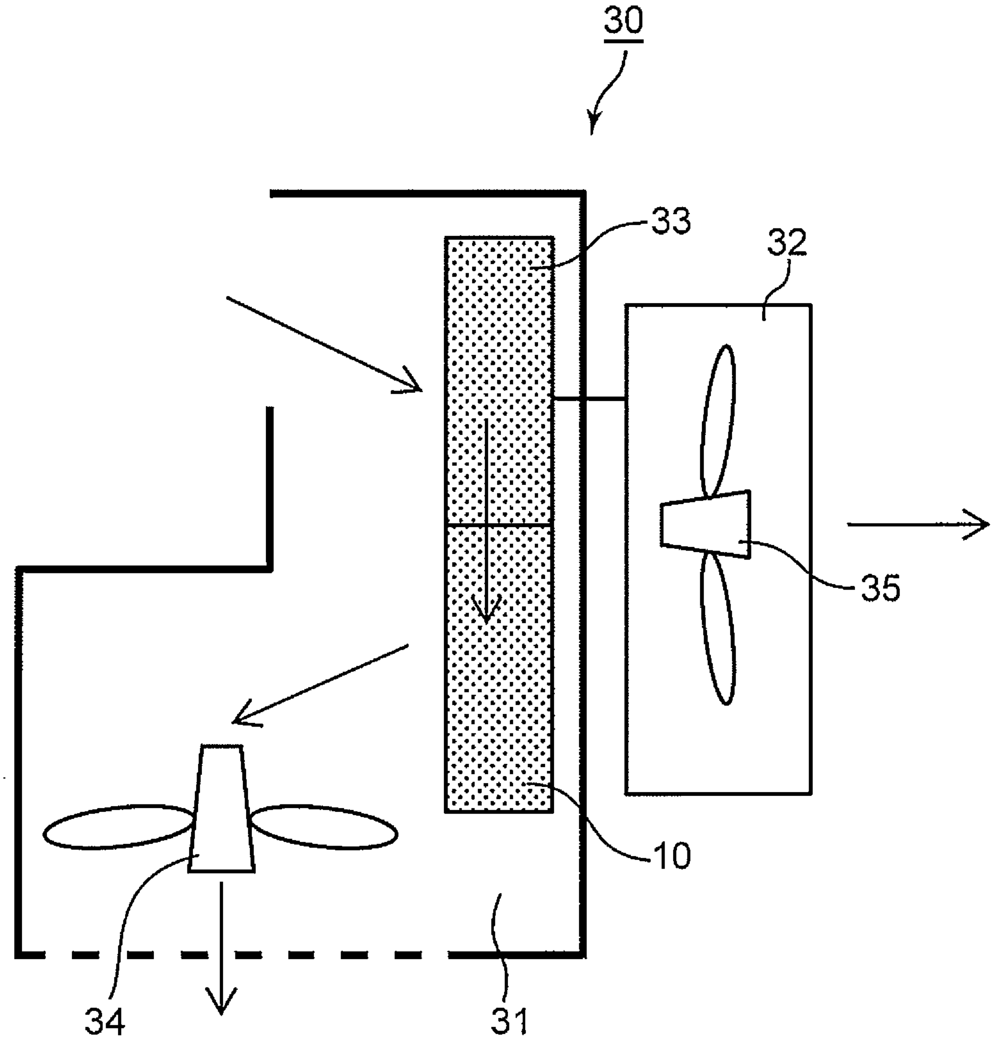
FIG. 3 is a schematic view illustrating a configuration of an air conditioner including the acidic gas separation device according to an embodiment of the present invention.

An air conditioner according to another embodiment of the present invention is an air conditioner including the acidic gas separation device. Examples of the air conditioner according to the present embodiment include an air conditioner 30 illustrated in FIG. 3, and the like. The air conditioner 30 includes an indoor unit 31 and an outdoor unit 32. The indoor unit 31 is not particularly limited as long as it includes the acidic gas separation device 10, and examples thereof include an indoor unit similar to an indoor unit of a general air conditioner except that the indoor unit includes the acidic gas separation device 10, and the like. The outdoor unit 32 is not particularly limited, and examples thereof include an outdoor unit of a general air conditioner, and the like. The indoor unit 31 includes a heat exchanger 33, the acidic gas separation device 10, and a fan 34. The heat exchanger 33 is not particularly limited as long as it operates together with the outdoor unit 32 and can adjust the air temperature by lowering (cooling) or raising (heating) the air temperature of the supplied gas such as air. Examples thereof include a heat exchanger provided in a general air conditioner, and the like. The fan 34 is not particularly limited as long as it can cause the gas from which the acidic gas has been removed by the acidic gas separation device 10 to flow to a place where the indoor unit 31 of the air conditioner 30 is installed (such as a room). The outdoor unit 32 cools or heats the temperature of the heated or cooled refrigerant or the like on the outdoor unit side when lowering (cooling) or raising (heating) the air temperature of the gas such as the air supplied to the heat exchanger 33 together with the heat exchanger 33. At this time, the fan 35 provided in the outdoor unit 32 discharges the gas in the outdoor unit 32 to the outside of the outdoor unit 32. The air conditioner 30 supplies air whose temperature has been adjusted by the heat exchanger 33 and the outdoor unit 32 to the acidic gas separation device 10, separates the acidic gas by the acidic gas separation device 10, and causes the gas from which the acidic gas has been separated to flow to a place where the indoor unit 31 of the air conditioner 30 is installed (such as room) by the fan 34. As a result, the air whose temperature has been adjusted and whose concentration of acidic gas has been reduced can be supplied to a place where the indoor unit 31 of the air conditioner 30 is installed (such as a room). That is, the air conditioner 30 can separate the acidic gas by acidic gas separation device 10, and can reduce the concentration of acidic gas contained in the gas such as air supplied from the air conditioner 30 by removing the separated acidic gas. The air conditioner is not particularly limited as long as the air conditioner includes the acidic gas separation device, and is not limited to the air conditioner that supplies gas such as air whose temperature has been adjusted to the acidic gas separation device 10 by the heat exchanger 33 and the outdoor unit 32 as described above. The air conditioner according to the present embodiment may be, for example, an air conditioner that supplies a gas from which an acidic gas has been removed by the acidic gas separation device to a heat exchanger and adjusts the air temperature of the gas by the heat exchanger and the outdoor unit.

An acidic gas concentration apparatus according to another embodiment of the present invention is an acidic gas concentration apparatus including the acidic gas separation device. Examples of the acidic gas concentration apparatus include the acidic gas separation device 10 illustrated in FIG. 1, and the like. FIG. 1 is also a schematic view illustrating a configuration of an acidic gas concentration apparatus including the acidic gas separation device according to an embodiment of the present invention. By the acidic gas separation device 10, a gas containing an acidic gas, such as air can be supplied to the first flow path 15, and a gas having an increased concentration of acidic gas can be released from the second flow path 16. When the gas (gas having an increased concentration of acidic gas) released from the second flow path 16 of the acidic gas separation device 10 is recovered, the acidic gas can be concentrated. Therefore, the acidic gas separation device 10 is an acidic gas concentration apparatus including the acidic gas separation device. Therefore, the acidic gas concentration apparatus can separate the acidic gas by the acidic gas separation device, and can concentrate the acidic gas by recovering the separated acidic gas. The acidic gas concentration apparatus may include the acidic gas separation device, and may include other members.

In such an acidic gas concentration apparatus, when the acidic gas is carbon dioxide, the apparatus can be applied as a carbon dioxide concentration apparatus. Demand for a carbon dioxide concentration apparatus is increasing in agricultural applications and the like. Specifically, the carbon dioxide concentration apparatus can be used for applications in which carbon dioxide in the air is concentrated and supplied to a vinyl house, thereby promoting the growth of the plant. In addition, the carbon dioxide concentration apparatus can also be used for CA storage applications in which carbon dioxide in the air is concentrated to increase the concentration of carbon dioxide in a storage compartment of a fruit or vegetable, thereby improving storage properties.

As described above, the present specification discloses various aspects of the technique, and the main techniques are summarized below.

One aspect of the present invention is an acidic gas separation device including: an electrolyte layer; a pair of electrodes provided with the electrolyte layer interposed between the pair of electrodes; and a voltage application unit that applies a voltage between the pair of electrodes, wherein the pair of electrodes are gas permeable electrodes, and the electrolyte layer contains: at least one selected from the group consisting of high molecular weight redox compounds having a radicalization rate of 90% or more, high molecular weight redox compounds having a quinone group in a molecule, and high molecular weight redox compounds having an imino group in a molecule; and a nonvolatile electrolytic solution.

With such a configuration, it is possible to provide an acidic gas separation device capable of easily separating an acidic gas from a gas containing an acidic gas and repeating the separation over a long period of time. The acidic gas separation device applies a voltage between a pair of electrodes such that the potential of one electrode is lower than the potential of the other electrode, for example. By applying the voltage in this manner, the high molecular weight redox compound contained in the electrolyte layer is electrolytically reduced to be a reductant on the side close to the one electrode having a low potential. It is considered that the acidic gas in contact with the surface of the electrolyte layer is bonded to the reductant and taken in the electrolyte layer. On the side close to the other electrode having a high potential, the high molecular weight redox compound contained in the electrolyte layer is electrolytically oxidized to be a radical or an oxidant. It is therefore considered that when the acidic gas is bonded to the high molecular weight redox compound, the acidic gas is desorbed from the high molecular weight redox compound and released from the electrolyte layer (the surface side of the other electrode side). It is therefore considered that the acidic gas separation device can take in carbon dioxide on the one electrode side and release carbon dioxide on the other electrode side. In the acidic gas separation device, since the redox compound contained in the electrolyte layer has a high molecular weight and the electrolytic solution is nonvolatile, it is considered that the acidic gas can be separated from the gas containing the acidic gas over a long period of time.

From the above, it is considered that the acidic gas can be easily separated from the gas containing the acidic gas, and this separation can be repeated over a long period of time.

In the acidic gas separation device, it is preferable that the pair of electrodes include a first electrode on a side in which an acidic gas is taken in from a gas containing an acidic gas, and a second electrode on a side in which an acidic gas is released from the electrolyte layer, and the voltage application unit apply a voltage between the pair of electrodes such that a potential of the first electrode is lower than a potential of the second electrode.

According to such a configuration, by only applying a voltage between the pair of electrodes (between the first electrode and the second electrode), the acidic gas can be continuously separated from the gas containing the acidic gas without inverting the voltage applied between the pair of electrodes. Incidentally, there is a possibility that volatilization of the electrolytic solution and the redox compound constituting the electrolyte layer is inhibited by continuously performing this separation (continuous operation). However, in the case of the acidic gas separation device, as described above, the redox compound contained in the electrolyte layer has a high molecular weight and the electrolytic solution is nonvolatile. Therefore, separation of the acidic gas from the gas containing the acidic gas can be continuously performed for a longer time. Consequently, the acidic gas separation device can more easily separate the acidic gas from the gas containing the acidic gas, and this separation can be repeated over a longer period of time.

In the acidic gas separation device, a thickness of the electrolyte layer is preferably 1 μm or more and 1,000 μm or less.

According to such a configuration, the acidic gas can be easily separated from the gas containing the acidic gas, and this separation can be repeated over a long period of time. Furthermore, the acidic gas separation device can be easily produced, and even when the voltage applied between the pair of electrodes is reduced, the acidic gas can be suitably separated from the gas containing the acidic gas.

In the acidic gas separation device, the electrolyte layer preferably further includes a support.

According to such a configuration, the electrolyte layer provided in the acidic gas separation device becomes an electrolyte layer in a suitable state such as high mechanical strength. Therefore, provision of this electrolyte layer in the acidic gas separation device allows the acidic gas to be easily separated from the gas containing the acidic gas, thereby making it possible to suitably obtain an acidic gas separation device capable of repeating this separation over a long period of time.

In the acidic gas separation device, a thickness of the support is preferably 1 μm or more and 1,000 μm or less.

According to such a configuration, since the electrolyte layer provided in the acidic gas separation device becomes an electrolyte layer in a more suitable state, the acidic gas separation device can be more suitably obtained.

In the acidic gas separation device, a difference obtained by subtracting the thickness of the support from the thickness of the electrolyte layer is preferably 1 μm or more and 500 μm or less.

According to such a configuration, the acidic gas can be more suitably separated from the gas containing the acidic gas. This is considered to be because in the acidic gas separation device, the adhesion between the electrode and the electrolyte layer is improved, and as a result, the transport efficiency of the acidic gas can be increased.

In the acidic gas separation device, a ratio of the thickness of the support to the thickness of the electrolyte layer is preferably 0.3 or more and 0.99 or less.

According to such a configuration, the acidic gas can be more suitably separated from the gas containing the acidic gas. This is considered to be because in the acidic gas separation device, the adhesion between the electrode and the electrolyte layer is improved, and as a result, the transport efficiency of the acidic gas can be increased. Furthermore, since the strength of the electrolyte layer provided in the acidic gas separation device can be increased, the acidic gas separation device can achieve both the maintenance of the strength of the electrolyte layer and the separation.

In the acidic gas separation device, a basis weight of the support is preferably 1 $g/m^2$ or more and 50 $g/m^2$ or less.

According to such a configuration, since the electrolyte layer provided in the acidic gas separation device becomes an electrolyte layer in a more suitable state, the acidic gas separation device can be more suitably obtained. This is considered to be because not only the degree of gas permeability of the support is high and components constituting the electrolyte layer such as a high molecular weight redox compound can be suitably loaded in the support, but also the mechanical strength of the electrolyte layer can be improved due to the high mechanical strength of the support.

In the acidic gas separation device, the support is preferably a nonwoven fabric.

According to such a configuration, since the electrolyte layer provided in the acidic gas separation device becomes an electrolyte layer in a more suitable state, the acidic gas separation device can be more suitably obtained. This is considered to be because when the support is a nonwoven fabric, it is excellent in terms of avoidance of complexity in the production process, maintenance of strength, and maintenance of flexibility.

In the acidic gas separation device, fibers constituting the nonwoven fabric preferably include at least one selected from the group consisting of polyolefin-based fibers, cellulose-based fibers, (meth)acrylic-based fibers, polyvinyl alcohol-based fibers, polyvinyl chloride-based fibers, polystyrene-based fibers, polyester-based fibers, polyamide-based fibers, polycarbonate-based fibers, and polyurethane-based fibers.

According to such a configuration, since the electrolyte layer provided in the acidic gas separation device becomes an electrolyte layer in a more suitable state, the acidic gas separation device can be more suitably obtained.

In the acidic gas separation device, a weight average molecular weight of the high molecular weight redox compound is preferably 1,000 or more.

According to such a configuration, the separation of the acidic gas from the gas containing the acidic gas can be repeated over a longer period of time.

In the acidic gas separation device, the high molecular weight redox compound having a radicalization rate of 90% or more preferably has a repeating unit represented by the following formula (1) in a molecule.

[Chemical Formula 2]

(1)

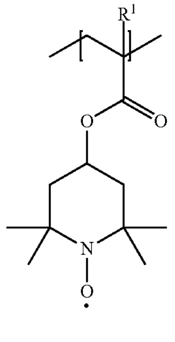

wherein $R^1$ represents a hydrogen atom or a methyl group.

According to such a configuration, the acidic gas can be more suitably separated from the gas containing the acidic gas.

An air purifier according to another aspect of the present invention is an air purifier including the acidic gas separation device.

According to such a configuration, the acidic gas can be separated from the gas containing the acidic gas by the acidic gas separation device, and the concentration of acidic gas contained in the gas supplied from the air purifier can be reduced by removing the separated acidic gas.

An air conditioner according to another aspect of the present invention is an air conditioner including the acidic gas separation device.

According to such a configuration, the acidic gas can be separated from the gas containing the acidic gas by the acidic gas separation device, and the concentration of acidic gas contained in the gas supplied from the air conditioner can be reduced by removing the separated acidic gas.

An acidic gas concentration apparatus according to another aspect of the present invention is an acidic gas concentration apparatus including the acidic gas separation device.

According to such a configuration, the acidic gas can be separated from the gas containing the acidic gas by the acidic gas separation device, and the acidic gas can be concentrated by recovering the separated acidic gas.

According to the present invention, it is possible to provide an acidic gas separation device capable of easily separating an acidic gas from a gas containing an acidic gas and repeating the separation over a long period of time, Specifically, when a gas containing an acidic gas is supplied to one electrode side, the acidic gas separation device can preferentially release the acidic gas from the other electrode side. According to the present invention, there are also provided an air purifier, an air conditioner, and an acidic gas concentration apparatus including the acidic gas separation device.

Hereinafter, the present invention will be specifically described with reference to Examples, but the present invention is not limited thereto.

EXAMPLES

Example 1

<Production of Acidic Gas Separation Device>

An acidic gas separation device having the structure illustrated in FIG. 1 was produced by the following procedure.

(Preparation of High Molecular Weight Redox Compound)

In an Erlenmeyer flask having an internal volume of 200 mL, 22.5 g (100 mmol) of 2,2,6,6-tetramethyl-4-piperidinyl methacrylate and 25 mL of methanol as a solvent were placed, and this was mixed to obtain a homogeneous solution. Then, 164 mg (1.00 mmol) of 2,2'-azobis-2,4-dimethylvaleronitrile as a polymerization initiator and 200 mL of methanol were placed in a 500 mL four-necked flask equipped with a stirrer, a nitrogen gas introduction tube, a thermometer, and a reflux condenser. The homogeneous solution was added to this solution, and the solution was mixed under stirring while being maintained at 25° C. Subsequently, oxygen in the reaction system was removed by purging with nitrogen gas, and then the reaction was carried out for 6 hours while the polymerization solution was maintained at 65° C. under stirring. After completion of the reaction, the reaction solution was cooled to room temperature, and 500 mL of water was added thereto. The solid obtained by filtration was washed with 300 mL of water and then with 500 mL of hexane, and dried under reduced pressure to obtain 22.0 g of a polymerization reaction product.

Next, 10 g of the polymerization reaction product obtained in the above process, 0.73 g (2.2 mmol) of sodium tungstate dihydrate as a catalyst, and 300 mL of methanol were charged into a 500 mL four-necked flask equipped with a stirrer, a nitrogen gas introduction tube, a thermometer, a reflux condenser, and a dropping funnel. Oxygen in the reaction system was removed by purging with nitrogen gas while the temperature was maintained at 25° C. Then, 25.2 g (222 mmol) of 30% hydrogen peroxide water was added dropwise to the mixture over 3 hours. Subsequently, the mixture was reacted at 40° C. for 8 hours. After completion of the reaction, the reaction solution was cooled to room temperature, and 500 mL of water was added thereto. The solid obtained by filtration was washed with 300 mL of water and dried under reduced pressure to obtain 10.2 g of a red solid. This red solid was a high molecular weight redox compound.

(Measurement of Weight Average Molecular Weight)

The obtained high molecular weight redox compound was measured by GPC under the following conditions using a gel permeation chromatography apparatus manufactured by Shimadzu Corporation, and as a result, the weight average molecular weight (Mw) was determined to be 79,000.

Column: Two tetrahydrofuran-based columns "KF-806M" connected in series (manufactured by Showa Denko K.K.)

Standard sample: Polymethyl methacrylate

Solvent and mobile phase: Tetrahydrofuran (THF) (concentration: 20 mM)

Flow rate: 1.0 mL/min

Temperature: 40° C.

Sample solution concentration: 0.2 wt % (filtered with a filter having an opening diameter of 0.45 μm)

Injection amount: 100 μL

Detector: RI (Measurement of Radicalization Rate by Chemical Titration Method)

The content of the repeating unit represented by the formula (1) in the high molecular weight redox compound was measured by a chemical titration method (oxidation-reduction titration method) based on an oxidation-reduction reaction, and the content (radicalization rate) of the formula (1) was calculated from the obtained content. Specifically, 100 mg of a sample (high molecular weight redox compound) was weighed and dissolved in chloroform and acetic acid, then a 0.2 N aqueous potassium iodide solution was added thereto, and the released iodine was back-titrated with a 0.05 N aqueous sodium thiosulfate solution to perform calculation. In the test, two specimens were analyzed, and the average value thereof was taken as an analysis value (radicalization rate). As a result, the radicalization rate of the obtained high molecular weight redox compound was 99%.

(Production of Support A)

A molten liquid crystal-forming wholly aromatic polyester composed of a copolymer of parahydroxybenzoic acid and 6-hydroxy-2-naphthoic acid was extruded by a twin-screw extruder, supplied to a meltblown nonwoven fabric production apparatus, and extruded at a single-hole discharge rate of 0.10 g/min and a resin temperature of 330° C., to obtain a nonwoven fabric having a basis weight of 15 $g/m^2$, and then the obtained nonwoven fabric was heated at 300° C. for 6 hours. Thereafter, the obtained nonwoven fabric was passed between a metal roll heated to 110° C. and a resin elastic roll, and further continuously treated by a pressurizing calender. The obtained meltblown nonwoven fabric had an average fiber diameter of 2.8 μm, a basis weight of 15 $g/m^2$ as described above, and a thickness of 25 μm. The obtained nonwoven fabric was used as a support A.

(Electrolyte Layer (Acidic Gas Separator))

First, the support A was fixed on a glass plate.

To 100.0 g of dimethylformamide (manufactured by FUJIFILM Wako Pure Chemical Corporation), 6.0 g of poly(vinylidene fluoride-co-hexafluoropropylene) (manufactured by Sigma-Aldrich Co. LLC.) was added, and the mixture was stirred at 80° C. for 3 hours for dissolution. Next, 2.00 g of a high molecular weight redox compound (high molecular weight redox compound having a radicalization rate of 90% or more) was added to the obtained solution, and the mixture was stirred at 80° C. for 1 hour for dissolution. Next, 12.0 g of an ionic liquid of [1-ethyl-3-methylimidazolium bis(fluorosulfonyl)imide (emimFSI, manufactured by Sigma-Aldrich Co. LLC.)] as a nonvolatile electrolytic solution was added to the obtained solution, and the mixed solution was heated to 40° C. and mixed with stirring for 3 hours. Using the liquid thus obtained, a liquid film having a thickness (coating thickness from a glass plate) of 600 μm was formed on the support A fixed on a glass plate by an applicator, and dried under reduced pressure at 60° C. for 8 hours. The dried film obtained by the drying was peeled off from the glass plate. By doing so, a dried film including a support and having a thickness of 50 μm was obtained as an electrolyte layer. The thickness of the support included in this electrolyte layer was 25 μm. The difference obtained by subtracting the thickness of the support from the thickness of the electrolyte layer was 25 μm. The ratio of the thickness of the support to the thickness of the electrolyte layer (thickness of support/thickness of electrolyte layer) was 0.5.

(Electrode)

A piece of carbon paper (TGP-H-030, manufactured by Toray Industries, Inc.) was cut into a size of 20 mm in length×20 mm in width×0.1 mm in thickness. A piece of conductive copper foil tape was attached to one surface of the cut carbon paper. Two of them were prepared and used as respective electrodes (cathode electrode and anode electrode).

(Flow Path)

A polytetrafluoroethylene resin plate was cut into a size of 50 mm in length×50 mm in width×5 mm in thickness, and two holes were made at appropriate positions in the resin plate. A groove having a depth of 1 mm×a length of 20 mm×a width of 20 mm connected to the holes was made in the cut resin plate. Two of them were prepared and used as respective flow paths (the first flow path and the second flow path).

(Acidic Gas Separation Device)

The electrolyte layer, the electrodes, and the flow paths were assembled so as to have the structure illustrated in FIG. 1, and a power supply as a voltage application unit was connected to the conductive copper foil tape of the electrodes. By doing so, an acidic gas separation device having the structure illustrated in FIG. 1 was produced.

<Evaluation>

The acidic gas separation device was evaluated by the following evaluation method. Here, evaluation was performed using carbon dioxide ($CO_2$) as the acidic gas. That is, a gas containing carbon dioxide was used as the gas containing the acidic gas.

First, the acidic gas separation device was installed in an environment of 25° C. Then, a 1 L gas bag filled with carbon dioxide so as to have a concentration of carbon dioxide of 2,000 ppm and an air pump were placed in the hole of the flow path on the cathode electrode side so that the carbon dioxide is circulated in the flow path on the cathode electrode side. In addition, a 1 L gas bag filled with carbon dioxide so as to have a concentration of carbon dioxide of 400 ppm and an air pump were placed in the hole of the flow path on the anode electrode side so that the carbon dioxide is circulated in the flow path on the anode electrode side. The concentration of carbon dioxide was measured with a portable carbon dioxide gas concentration meter (FUSO-77535, manufactured by FUSO Co., Ltd.) placed in each of the gas bag. Then, a voltage of 3.0 V was applied between the electrodes by adjusting the power supply. After the voltage was applied, the gas in the gas bag was circulated in the flow path of each electrode at a flow rate of 500 mL/min by the air pump mounted to each of the flow path on the cathode electrode side and the flow path on the anode electrode side. By doing so, the gas in the gas bag was continued to flow through the flow path of each electrode at a flow rate of 500 mL/min. The concentration of carbon dioxide after 60 minutes was measured. As a result, the concentration of carbon dioxide in the flow path on the cathode electrode side was 150 ppm. This evaluation test was repeated 10 times for the same electrolyte film, and the concentration of carbon dioxide in the flow path on the cathode electrode side after the 10th evaluation test was completed was 160 ppm. The results are shown in Table 1.

Example 2

A high molecular weight redox compound was prepared in the same manner as in Example 1 except that 268 mg (2.00 mmol) of 2,2'-azobis-2,4-dimethylvaleronitrile was used as a polymerization initiator, toluene was used in place of methanol, and the reaction was performed for 3 hours while the temperature of the polymerization solution was maintained at 65° C., instead of performing the reaction for 6 hours while the temperature of the polymerization solution was maintained at 110° C. The weight average molecular weight of the obtained high molecular weight redox compound was 2,100 as measured by the same method as in Example 1. The radicalization rate of the high molecular weight redox compound was 98 mass % as measured by the same method as in Example 1.

An acidic gas separation device was produced in the same manner as in Example 1 except that the obtained high molecular weight redox compound (high molecular weight redox compound having a radicalization rate of 90% or more) was used. The thickness of the electrolyte layer included in the acidic gas separation device was 50 μm. The thickness of the support included in the electrolyte layer was 25 m. The difference obtained by subtracting the thickness of the support from the thickness of the electrolyte layer was 25 m. The ratio of the thickness of the support to the thickness of the electrolyte layer (thickness of support/thickness of electrolyte layer) was 0.5. Then, the same evaluation as in Example 1 was performed using the obtained acidic gas separation device. The results are shown in Table 1.

Example 3

A high molecular weight redox compound was prepared in the same manner as in Example 1 except that 55 mg (0.67 mmol) of 2,2'-azobis-2,4-dimethylvaleronitrile was used as a polymerization initiator, and the polymerization solution was reacted for 12 hours instead of being reacted for 6 hours. The weight average molecular weight of the obtained high molecular weight redox compound was 310,000 as measured by the same method as in Example 1. The radicalization rate of the high molecular weight redox compound was 97% as measured by the same method as in Example 1.

An acidic gas separation device was produced in the same manner as in Example 1 except that the obtained high molecular weight redox compound (high molecular weight redox compound having a radicalization rate of 90% or more) was used. The thickness of the electrolyte layer included in the acidic gas separation device was 50 μm. The thickness of the support included in the electrolyte layer was 25 μm. The difference obtained by subtracting the thickness of the support from the thickness of the electrolyte layer was 25 μm. The ratio of the thickness of the support to the thickness of the electrolyte layer (thickness of support/thickness of electrolyte layer) was 0.5. Then, the same evaluation as in Example 1 was performed using the obtained acidic gas separation device. The results are shown in Table 1.

Example 4

In a three-necked flask having an internal volume of 50 mL, 1.51 g (5.45 mmol) of 1,4-dichloroanthraquinone and 20 mL of dehydrated dimethylformamide were placed, and this was mixed under nitrogen to obtain a homogeneous solution. Next, in a 300 mL four-necked flask equipped with a stirrer, a nitrogen gas introduction tube, a thermometer, and a reflux condenser, 1.51 g (5.45 mmol) of 1,4-dichloroanthraquinone, 1.13 g (7.27 mmol) of bis(1,5-cyclooctadiene)nickel(0) 2,2'bipyridyl, 590 mg (5.45 mmol) of 1,5-cyclooctadiene, and 50 mL of dehydrated dimethylformamide were mixed under nitrogen, and the homogeneous solution was added dropwise to the mixed solution over 30 minutes while the temperature of the mixed solution was maintained at 65° C. The reaction solution was reacted at 65° C. for 48 hours, then the reaction solution was cooled to room temperature, 100 mL of 1 M hydrochloric acid was added thereto, and the mixture was stirred at room temperature for 1 hour. The solid obtained by filtration was washed with 200 mL of 1 M hydrochloric acid, 200 mL of ion-exchanged water twice, 100 mL of DMF twice, and 100 mL of ion-exchanged water in this order, and dried under reduced pressure to obtain 0.78 g of a yellow solid (yield: 63%). This yellow solid was a high molecular weight redox compound (high molecular weight redox compound having a quinone group in the molecule). The weight average molecular weight of the obtained high molecular weight redox compound was 140,000 as measured by the same method as in Example 1.

An acidic gas separation device was produced in the same manner as in Example 1 except that the obtained high molecular weight redox compound (high molecular weight redox compound having a quinone group in the molecule) was used. The thickness of the electrolyte layer included in the acidic gas separation device was 50 μm. The thickness of the support included in the electrolyte layer was 25 μm. The difference obtained by subtracting the thickness of the support from the thickness of the electrolyte layer was 25 μm. The ratio of the thickness of the support to the thickness of the electrolyte layer (thickness of support/thickness of electrolyte layer) was 0.5. Then, the same evaluation as in Example 1 was performed using the obtained acidic gas separation device. The results are shown in Table 1.

Example 5

A high molecular weight redox compound was prepared in the same manner as in Example 1 except that 11 mg (0.067 mmol) of 2,2'-azobis-2,4-dimethylvaleronitrile was used as a polymerization initiator, and the polymerization solution was reacted for 24 hours instead of being reacted for 6 hours. The weight average molecular weight of the obtained high molecular weight redox compound was 1,490,000 as measured by the same method as in Example 1. The radicalization rate of the high molecular weight redox compound was 93 mass % as measured by the same method as in Example 1.

An acidic gas separation device was produced in the same manner as in Example 1 except that the obtained high molecular weight redox compound (high molecular weight redox compound having a radicalization rate of 90% or more) was used. The thickness of the electrolyte layer included in the acidic gas separation device was 50 μm. The thickness of the support included in the electrolyte layer was 25 μm. The difference obtained by subtracting the thickness of the support from the thickness of the electrolyte layer was 25 μm. The ratio of the thickness of the support to the thickness of the electrolyte layer (thickness of support/thickness of electrolyte layer) was 0.5. Then, the same evaluation as in Example 1 was performed using the obtained acidic gas separation device. The results are shown in Table 1.

Example 6

A high molecular weight redox compound was prepared in the same manner as in Example 1 except that 99 mg (0.50 mmol) of ethylene glycol dimethacrylate was used in addition to 22.5 g (100 mmol) of 2,2,6,6-tetramethyl-4-piperidinyl methacrylate. The radicalization rate of the obtained high molecular weight redox compound was 93 mass % as measured by the same method as in Example 1.

An acidic gas separation device was produced in the same manner as in Example 1 except that the obtained high molecular weight redox compound (high molecular weight redox compound having a radicalization rate of 90% or more) was ground in a mortar, and then sieved with a sieve having a mesh size of 20 μm. The thickness of the electrolyte layer included in the acidic gas separation device was 50 μm. The thickness of the support included in the electrolyte layer was 25 μm. The difference obtained by subtracting the thickness of the support from the thickness of the electrolyte layer was 25 μm. The ratio of the thickness of the support to the thickness of the electrolyte layer (thickness of support/thickness of electrolyte layer) was 0.5. Then, the same evaluation as in Example 1 was performed using the obtained acidic gas separation device. The results are shown in Table 1. The obtained high molecular weight redox compound was insoluble in tetrahydrofuran, and therefore the weight average molecular weight thereof was not measurable.

Example 7

In Example 1, a liquid film having a coating thickness (coating thickness from a glass plate) of 300 μm was formed on a support fixed on a glass plate, and dried under reduced pressure at 60° C. for 8 hours. The dried film obtained by the drying was peeled off from the glass plate. By doing so, a dried film including a support and having a thickness of 25 μm was obtained as an electrolyte layer. An acidic gas separation device was produced in the same manner as in Example 1 except for using the electrolyte film thus obtained. Note that the thickness of the support included in this electrolyte layer was 25 μm. The difference obtained by subtracting the thickness of the support from the thickness of the electrolyte layer was 0 μm, and the ratio of the thickness of the support to the thickness of the electrolyte layer was 1. Then, the same evaluation as in Example 1 was performed using the obtained acidic gas separation device. The results are shown in Table 1.

Example 8

(Production of Support B)

A slurry was produced by dispersing, in water, 75 wt % of 1.2 dtex×3 mm polyvinyl alcohol-based fiber (vinylon, manufactured by Kuraray Co., Ltd., VPB103×3) and 25 wt % of 1.1 dtex×3 mm polyvinyl alcohol-based binder fiber (vinylon binder, manufactured by Kuraray Co., Ltd.: VPB105-1×3). Paper was made using the slurry by a papermaking machine and dried by a Yankee dryer, to obtain a substrate (support B) having a basis weight of 38.0 g/m$^2$ and a thickness of 220 μm.

In Example 1, the support A was changed to the support B, a liquid film was formed on the support (support B) fixed on a glass plate with a coating thickness (coating thickness from the surface of the support on the glass plate) of 220 μm, and dried under reduced pressure at 60° C. for 1 hour. This operation was repeated 4 times, and the resulting film was finally dried under reduced pressure at 60° C. for 8 hours, and the dried film obtained by the drying was peeled off from the glass plate. By doing so, a dried film including a support and having a thickness of 220 μm was obtained as an electrolyte layer. An acidic gas separation device was produced in the same manner as in Example 1 except for using the electrolyte film thus obtained. The thickness of the support included in the electrolyte layer was 220 μm. The difference obtained by subtracting the thickness of the support from the thickness of the electrolyte layer was 0 μm, and the ratio of the thickness of the support to the thickness of the electrolyte layer was 1. Then, the same evaluation as in Example 1 was performed using the obtained acidic gas separation device. The results are shown in Table 1.

Example 9

(Production of Support C)

A slurry was produced by dispersing, in water, 75 wt % of 1.2 dtex×3 mm polyvinyl alcohol-based fiber (vinylon, manufactured by Kuraray Co., Ltd., VPB103×3) and 25 wt % of 1.1 dtex×3 mm polyvinyl alcohol-based binder fiber (vinylon binder, manufactured by Kuraray Co., Ltd.: VPB105-1×3). Paper was made using the slurry by a papermaking machine and dried by a Yankee dryer, to obtain a substrate (support C) having a basis weight of 78.0 g/m$^2$ and a thickness of 450 μm.

In Example 1, the support A was changed to the support C, and a liquid film having a coating thickness (coating thickness from the surface of the support on the glass plate) of 220 μm was formed on the support (support C) fixed on the glass plate, and dried under reduced pressure at 60° C. for 1 hour. This operation was repeated 4 times, and the resulting film was finally dried under reduced pressure at 60° C. for 8 hours, and the dried film obtained by the drying was peeled off from the glass plate. By doing so, a dried film including a support and having a thickness of 510 μm was obtained as an electrolyte layer. An acidic gas separation device was produced in the same manner as in Example 1 except for using the electrolyte film thus obtained. The thickness of the support included in the electrolyte layer was 450 m. The difference obtained by subtracting the thickness of the support from the thickness of the electrolyte layer was 60 m, and the ratio of the thickness of the support to the thickness of the electrolyte layer was about 0.9 (=450/510).

Then, the same evaluation as in Example 1 was performed using the obtained acidic gas separation device. The results are shown in Table 1.

Example 10

A high molecular weight redox compound was prepared in the same manner as in Example 1 except that 55 mg (0.67 mmol) of 2,2'-azobis-2,4-dimethylvaleronitrile was used as a polymerization initiator, and the polymerization solution was reacted for 12 hours instead of being reacted for 6 hours. The weight average molecular weight of the obtained high molecular weight redox compound was 310,000 as measured by the same method as in Example 1. The radicalization rate of the high molecular weight redox compound was 97% as measured by the same method as in Example 1.

An acidic gas separation device was produced using the obtained high molecular weight redox compound (high molecular weight redox compound having a radicalization rate of 90% or more) in the same manner as in Example 1 except that a support was not used. The thickness of the electrolyte film was 24 m. Then, the same evaluation as in Example 1 was performed using the obtained acidic gas separation device. The results are shown in Table 1.

Comparative Example 1

An acidic gas separation device was produced in the same manner as in Example 1 except that 2,2,6,6-tetramethyl-4-piperidinyl methacrylate was used in place of the high molecular weight redox compound. Then, the same evaluation as in Example 1 was performed using the obtained acidic gas separation device. The results are shown in Table 1.

Comparative Example 2

An acidic gas separation device was produced in the same manner as in Example 1 except that bis(2,2,6,6-tetramethyl-4-piperidyl) adipate was used in place of the high molecular weight redox compound. Then, the same evaluation as in Example 1 was performed using the obtained acidic gas separation device. The results are shown in Table 1.

Comparative Example 3

A high molecular weight redox compound was prepared in the same manner as in Example 1 except that the amount of hydrogen peroxide used was 20 g in Example 1. The weight average molecular weight of the obtained high molecular weight redox compound was 79,000 as measured by the same method as in Example 1. The radicalization rate of the obtained high molecular weight redox compound was 78 mass % as measured by the same method as in Example 1. The same procedures as in Example 1 were carried out.

An acidic gas separation device was produced in the same manner as in Example 1 except for using the obtained high molecular weight redox compound (high molecular weight redox compound having a radicalization rate of less than 90%). Then, the same evaluation as in Example 1 was performed using the obtained acidic gas separation device. The results are shown in Table 1.

Comparative Example 4

A high molecular weight redox compound was prepared in the same manner as in Example 1 except that the amount of hydrogen peroxide used was 22.5 g in Example 1. The weight average molecular weight of the obtained high molecular weight redox compound was 79,000 as measured by the same method as in Example 1. The radicalization rate of the obtained high molecular weight redox compound was 89 mass % as measured by the same method as in Example 1. The same procedures as in Example 1 were carried out.

An acidic gas separation device was produced in the same manner as in Example 1 except for using the obtained high molecular weight redox compound (high molecular weight redox compound having a radicalization rate of less than 90%). Then, the same evaluation as in Example 1 was performed using the obtained acidic gas separation device. The results are shown in Table 1.

In Table 1, the symbol "-" in the column of the weight average molecular weight indicates that the weight average molecular weight could not be measured because the redox compound was insoluble in tetrahydrofuran. The symbol "-" in the column of the radicalization rate also indicates that the radicalization rate could not be measured.

TABLE 1

| | Redox compound | | $CO_2$ concentration after 60 minutes of separation (ppm) | |
|---|---|---|---|---|
| | Weight average molecular weight | Radicalization rate (%) | 1st evaluation test | 10th evaluation test |
| Example 1 | 79,000 | 99 | 150 | 160 |
| Example 2 | 2,100 | 98 | 80 | 120 |
| Example 3 | 310,000 | 97 | 250 | 280 |
| Example 4 | 140,000 | — | 300 | 330 |
| Example 5 | 1,490,000 | 93 | 1,010 | 1,340 |
| Example 6 | — | 92 | 970 | 1,220 |
| Example 7 | 79,000 | 99 | 45 | 45 |
| Example 8 | 79,000 | 99 | 320 | 360 |
| Example 9 | 79,000 | 99 | 610 | 790 |
| Example 10 | 310,000 | 97 | 240 | 250 |
| Comparative Example 1 | 240 | 0 | 1,260 | 2,000 |
| Comparative Example 2 | 456 | 0 | 490 | 1,780 |
| Comparative Example 3 | 79,000 | 78 | 1,320 | 1,340 |
| Comparative Example 4 | 79,000 | 89 | 1,270 | 1,300 |

As can be seen from Table 1, in the acidic gas separation devices (Examples 1 to 10) in which the electrolyte layer containing the high molecular weight redox compound is sandwiched between the pair of electrodes, the redox compound being a compound in which the acidic gas is adsorbed by the electrolytic reduction and is desorbed by the electrolytic oxidation, the acidic gas could be more separated from the gas containing the acidic gas even when the separation was repeated, as compared with the case of using the low molecular weight redox compounds (Comparative Examples 1 and 2). In the acidic gas separation devices according to Examples 1 to 3 and 5 to 10 in which the high molecular weight redox compound having a radicalization rate of 90% or more was used, the acidic gas could be more separated from the gas containing the acidic gas even when the separation was repeated, as compared with the ease of using the high molecular weight redox compound having a radicalization rate of less than 90% (Comparative Example 3) or as compared with the case of using the high molecular weight redox compound having a radicalization rate of slightly less than 90% (Comparative Example 4). In the acidic gas separation device according to Example 5, although the molecular weight of the used high molecular weight redox compound was increased and the initial separation efficiency was reduced, the initial separation was good as compared with the case of using a high molecular weight redox compounds having a radicalization rate of less than 90% (Comparative Examples 3 and 4), and even when the separation was repeated, the acidic gas was separated from the gas containing the acidic gas to the same extent as in Comparative Examples 3 and 4. In the acidic gas separation device according to Example 4 in which the high molecular weight redox compound having a quinone group in the molecule was used, the initial separation was good as compared with the case of using the high molecular weight redox compounds having a radicalization rate of less than 90% (Comparative Examples 3 and 4), and the acidic gas could be more separated from the gas containing the acidic gas even when the separation was repeated.

In Example 1, when an attempt is made to produce an acidic gas separation device without using a support, a suitable electrolyte layer cannot be obtained in some cases. Specifically, in Example 1, a liquid film having a thickness of 200 μm was formed on a glass plate by an applicator without using a support, dried under reduced pressure at 60° C. for 8 hours, and the dried film obtained by the drying was peeled off from the glass plate. By doing so, a dried film having a thickness of 15 μm was obtained as an electrolyte layer. On the other hand, when the electrolyte layer is peeled off from the glass plate, the electrolyte layer was broken in some cases. For this reason, an acidic gas separation device was not produced in some cases. From this, although there is a case where the acidic gas separation device can be produced even without a support (also in this case, there is a case where the acidic gas separation device can be produced, and the above-described Example 10 and the like are an example of this case), it was found that the electrolyte layer preferably includes a support from the viewpoint of mechanical strength of the electrolyte layer and the like. When the acidic gas separation device could be produced, the obtained acidic gas separation device could suitably separate the acidic gas from the gas containing the acidic gas.

This application is based on Japanese Patent Application No. 2020-123383 filed on Jul. 20, 2020, the contents of which are incorporated in the present application.

Although the present invention has been appropriately and sufficiently described above through the embodiments in order to express the present invention, it should be recognized that a person skilled in the art can easily modify and/or improve the above-described embodiments. Therefore, unless a change or improvement made by a person skilled in the art is at a level that departs from the scope of the claims described in the claims, the change or improvement is interpreted to be included in the scope of the claims.

INDUSTRIAL APPLICABILITY

According to the present invention, there is provided an acidic gas separation device capable of easily separating an acidic gas from a gas containing the acidic gas and repeating the separation over a long period of time. According to the present invention, there are also provided an air purifier, an air conditioner, and an acidic gas concentration apparatus including the acidic gas separation device.

The invention claimed is:

1. An acidic gas separation device comprising:

an electrolyte layer;

a pair of electrodes provided with the electrolyte layer interposed between the pair of electrodes; and a voltage application unit that applies a voltage between the pair of electrodes, wherein the pair of electrodes are gas permeable electrodes, and the electrolyte layer contains a high molecular weight redox compound having a radicalization rate of 90% or more and a nonvolatile electrolytic solution.

2. The acidic gas separation device according to claim 1, wherein the pair of electrodes include a first electrode on a side in which an acidic gas is taken in from a gas containing the acidic gas and a second electrode on a side in which the acidic gas is released from the electrolyte layer, and the voltage application unit applies the voltage between the pair of electrodes such that a potential of the first electrode is lower than a potential of the second electrode.

3. The acidic gas separation device according to claim 1, wherein a thickness of the electrolyte layer is 1 μm or more and 1,000 μm or less.

4. The acidic gas separation device according to claim 1, wherein the electrolyte layer further includes a support.

5. The acidic gas separation device according to claim 4, wherein a thickness of the support is 1 μm or more and 1,000 μm or less.

6. The acidic gas separation device according to claim 4, wherein a difference between a thickness of the support and a thickness of the electrolyte layer is 1 μm or more and 500 μm or less.

7. The acidic gas separation device according to claim 4, wherein a thickness ratio of the support to the electrolyte layer is 0.3 or more and 0.99 or less.

8. The acidic gas separation device according to claim 4, wherein a basis weight of the support is 1 $g/m^2$ or more and 50 $g/m^2$ or less.

9. The acidic gas separation device according to claim 4, wherein the support is a nonwoven fabric.

10. The acidic gas separation device according to claim 9, wherein fibers constituting the nonwoven fabric include at least one selected from the group consisting of polyolefin-based fibers, cellulose-based fibers, (meth)acrylic-based fibers, polyvinyl alcohol-based fibers, polyvinyl chloride-based fibers, polystyrene-based fibers, polyester-based fibers, polyamide-based fibers, polycarbonate-based fibers, and polyurethane-based fibers.

11. The acidic gas separation device according to claim 1, wherein a weight average molecular weight of the high molecular weight redox compound is 1,000 or more.

12. The acidic gas separation device according to claim 1, wherein the high molecular weight redox compound having a radicalization rate of 90% or more has a repeating unit represented by the following formula (1):

(1)
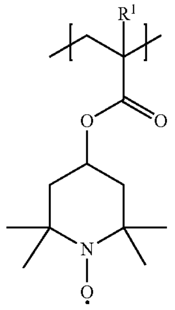
wherein $R^1$ represents a hydrogen atom or a methyl group.
13. An air purifier comprising the acidic gas separation device according to claim 1.
14. An air conditioner comprising the acidic gas separation device according to claim 1.
15. An acidic gas concentration apparatus comprising the acidic gas separation device according to claim 1.
* * * * *